United States Patent
Wang et al.

(10) Patent No.: US 11,419,918 B2
(45) Date of Patent: Aug. 23, 2022

(54) TREATMENT OF BILIARY CIRRHOSIS BASED ON OXYNTOMODULIN ANALOGUE GLP-1R/GCGR DUAL-TARGET AGONIST PEPTIDE

(71) Applicant: Shenzhen Turier Biotech Co., Ltd., Shenzhen (CN)

(72) Inventors: Lei Wang, Shenzhen (CN); Jianmei Ouyang, Shenzhen (CN)

(73) Assignee: SHENZHEN TURIER BIOTECH CO., LTD.

( * ) Notice: Subject to any disclaimer, the term of this patent is extended or adjusted under 35 U.S.C. 154(b) by 0 days.

(21) Appl. No.: 16/760,894

(22) PCT Filed: Oct. 19, 2018

(86) PCT No.: PCT/CN2018/111030
§ 371 (c)(1),
(2) Date: Apr. 30, 2020

(87) PCT Pub. No.: WO2019/085772
PCT Pub. Date: May 9, 2019

(65) Prior Publication Data
US 2021/0187074 A1    Jun. 24, 2021

(30) Foreign Application Priority Data
Nov. 6, 2017 (CN) .......................... 201711079272.5

(51) Int. Cl.
*A61K 38/00* (2006.01)
*A61K 38/26* (2006.01)
*A61P 1/16* (2006.01)

(52) U.S. Cl.
CPC ................ *A61K 38/26* (2013.01); *A61P 1/16* (2018.01)

(58) Field of Classification Search
CPC ........... A61K 38/26; A61K 38/16; A61P 1/16; C07K 14/605
See application file for complete search history.

(56) References Cited

U.S. PATENT DOCUMENTS

2017/0183383 A1    6/2017  Jiang

FOREIGN PATENT DOCUMENTS

| CN | 104926934 A | 9/2015 |
| CN | 106046145 A | 10/2016 |
| CN | 104926934 B | 11/2016 |
| CN | 106519015 A | 3/2017 |
| CN | 107106660 A | 8/2017 |
| WO | WO2004071393 A2 | 8/2004 |
| WO | WO2006005469 A2 | 1/2006 |
| WO | WO2014017843 A1 | 1/2014 |
| WO | WO2017110425 A1 | 6/2017 |
| WO | WO2017181452 A1 | 10/2017 |

OTHER PUBLICATIONS

Goke et al. GLP-1 analogues: a new therapeutic approach to prevent ductopenia in cholangiopathies? Gut Jul. 2009 vol. 58 No. 7 (Year: 2009).*
Johns Hopkins Accessed Jul. 13, 2021 at https://www.hopkinsmedicine.org/health/conditions-and-diseases/biliary-cirrhosis-bile-duct-cancer. (Year: 2021).*
English translation of CN106046145A provided by Google patents (Year: 2016).*
Angulo, P.et al. Liver fibrosis, but no other histologic features, is associated with long-term outcomes of patients with nonalcoholic fatty liver disease. Gastroenterology, 2015, 149, 389-397.e10.
Liu Ling, Research Status of Animal Models of Bile Duct Ligation (BDL)-Induced Hepatic Fibrosis, Chongqing Medical Journal, 2013, 8, 2793-2796.
Shen H, Fan Y, Yang X, et al. Increased expression of cystic fibrosis transmembrance conductance regulator in rat liver after common bile duct ligation. J Cell Physiol, 2005, 203, 599-603.
Qin Dongmei, Zhao Wenhui, Hu Liping, etc. Research on Rat Hepatic Fibrosis Model Established by Bile Duct Ligation Operation, Lishizhen Med Mater Med Res, 2012, 23, 803-805.
Kazuyoshi et al. Death receptor 5 mediated-apoptosis contributes to cholestasis liver disease. PNAS, 2008, 10895-10900.
Liu Songtao, Liao Huiyu. Clinical Study and Progress of Obeticholic Acid, Beijing Medical Journal, 2015, 37, 1174-1176.
Kowdley KV, Jones D, Luketic V, et al. An international study evaluating the farnesoid X receptor agonist obeticholic acid as monotherapy in PBC. J. Hepatol, 2011, 54, 13.
European Search Report dated Jul. 20, 2021, in related EP patent application No. 18873776.1.
Gossard AA, Gores GJ PPAR agonists for primary biliary cholangitis. Lancet Gastroenterol Hepatol. Oct. 2017;2(10):693-694.doi:10.1016/S2468-1253(17)30256-X.
Oo, Y.H., Neuberger, J. Options for Treatment of Primary Biliary Cirrhosis. Drugs 64, 2261-2271 (2004). https://doi.org/10.2165/00003495-200464200-00001.

* cited by examiner

*Primary Examiner* — Aradhana Sasan
*Assistant Examiner* — Mercy H Sabila
(74) *Attorney, Agent, or Firm* — Maschoff Brennan

(57) ABSTRACT

The invention relates to uses of polypeptide compounds having dual target agonist effect on glucagon-like peptide-1 receptor (GLP-1R) and glucagon receptor (GCGR), characterized by high enzymolysis stability, high biological activity and no adverse reaction. The polypeptide compounds are able to significantly improve a degree of BDL-induced cholestasis hepatic fibrosis in rats, and have significant therapeutic effects on diseases such as biliary cirrhosis. The dual target agonist polypeptides are applicable to the prevention or treatment of biliary cirrhosis and related hepatic fibrosis diseases.

11 Claims, 5 Drawing Sheets

Specification includes a Sequence Listing.

SEQUENCE LISTING

<160> NUMBER OF SEQ ID NOS: 49

<210> SEQ ID NO 1
<211> LENGTH: 40
<212> TYPE: PRT
<213> ORGANISM: Artificial
<220> FEATURE:
<223> OTHER INFORMATION: Compound 1
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 1

His Ser Gln Gly Thr Phe Thr Ser Asp Tyr Ser Lys Lys Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 2
<211> LENGTH: 40
<212> TYPE: PRT
<213> ORGANISM: Artificial
<220> FEATURE:
<223> OTHER INFORMATION: Compound 2
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 2

His Ser Gln Gly Thr Phe Thr Ser Asp Tyr Ser Lys Lys Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 3
<211> LENGTH: 40
<212> TYPE: PRT
<213> ORGANISM: Artificial
<220> FEATURE:
<223> OTHER INFORMATION: Compound 3
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 3

His Ser Gln Gly Thr Phe Thr Ser Asp Tyr Ser Lys Lys Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Ser
         35                  40

<210> SEQ ID NO 4
<211> LENGTH: 40
<212> TYPE: PRT
<213> ORGANISM: Artificial
<220> FEATURE:
<223> OTHER INFORMATION: Compound 4
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 4

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Ser
         35                  40

<210> SEQ ID NO 5
<211> LENGTH: 40
<212> TYPE: PRT
<213> ORGANISM: Artificial
<220> FEATURE:
<223> OTHER INFORMATION: Compound 5
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 5

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Ser
         35                  40

<210> SEQ ID NO 6
<211> LENGTH: 40
<212> TYPE: PRT
<213> ORGANISM: Artificial
<220> FEATURE:
<223> OTHER INFORMATION: Compound 6
<220> FEATURE:
<221> NAME/KEY: MISC_FEATURE
<222> LOCATION: (2)..(2)
<223> OTHER INFORMATION: D-Ser

<400> SEQUENCE: 6

His Ser Gln Gly Thr Phe Thr Ser Asp Tyr Ser Lys Tyr Leu Asp Lys
1               5                   10                  15

Arg Arg Ala Gln Asp Phe Val Gln Trp Leu Met Asn Thr Gly Gly Pro
            20                  25                  30

Ser Ser Gly Ala Pro Pro Ser

-continued

```
<210> SEQ ID NO 7
<211> LENGTH: 40
<212> TYPE: PRT
<213> ORGANISM: Artificial
<220> FEATURE:
<223> OTHER INFORMATION: Compound 7
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 7

His Ser Gln Gly Thr Phe Thr Ser Asp Tyr Ser Lys Tyr Leu Asp Xaa
1               5                   10                  15

Lys Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 8
<211> LENGTH: 39
<212> TYPE: PRT
<213> ORGANISM: Artificial
<220> FEATURE:
<223> OTHER INFORMATION: Compound 8
<220> FEATURE:
<221> NAME/KEY: MISC_FEATURE
<222> LOCATION: (2)..(2)
<223> OTHER INFORMATION: X=Aib
<220> FEATURE:
<221> NAME/KEY: MISC_FEATURE
<222> LOCATION: (16)..(16)
<223> OTHER INFORMATION: X=Aib

<400> SEQUENCE: 8

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Leu Asp Gly Gly Pro Ser
            20                  25                  30

Ser Gly Ala Pro Pro Pro Ser
        35

<210> SEQ ID NO 9
<211> LENGTH: 40
<212> TYPE: PRT
<213> ORGANISM: Artificial
<220> FEATURE:
<223> OTHER INFORMATION: Compound 9
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 9

His Ser Gln Gly Thr Phe Thr Ser Asp Tyr Ser Lys Lys Leu Asp Xaa
1               5                   10                  15

Arg Arg Ala Gln Asp Phe Val Gln Trp Leu Met Asn Thr Gly Gly Pro
            20                  25                  30
```

```
Ser Ser Gly Ala Pro Pro Pro Ser
        35                  40

<210> SEQ ID NO 10
<211> LENGTH: 40
<212> TYPE: PRT
<213> ORGANISM: Artificial
<220> FEATURE:
<223> OTHER INFORMATION: Compound 10
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 10

His Ser Gln Gly Thr Phe Thr Ser Asp Tyr Ser Lys Tyr Leu Asp Xaa
1               5                   10                  15

Lys Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 11
<211> LENGTH: 39
<212> TYPE: PRT
<213> ORGANISM: Artificial
<220> FEATURE:
<223> OTHER INFORMATION: Compound 11
<220> FEATURE:
<221> NAME/KEY: MISC_FEATURE
<222> LOCATION: (2)..(2)
<223> OTHER INFORMATION: X=Aib
<220> FEATURE:
<221> NAME/KEY: MISC_FEATURE
<222> LOCATION: (16)..(16)
<223> OTHER INFORMATION: X=Aib

<400> SEQUENCE: 11

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Leu Asp Gly Gly Pro Ser
            20                  25                  30

Ser Gly Ala Pro Pro Pro Ser
        35

<210> SEQ ID NO 12
<211> LENGTH: 39
<212> TYPE: PRT
<213> ORGANISM: Artificial
<220> FEATURE:
<223> OTHER INFORMATION: Compound 12
<220> FEATURE:
<221> NAME/KEY: MISC_FEATURE
<222> LOCATION: (2)..(2)
<223> OTHER INFORMATION: X=Aib
<220> FEATURE:
<221> NAME/KEY: MISC_FEATURE
<222> LOCATION: (16)..(16)
<223> OTHER INFORMATION: X=Aib

<400> SEQUENCE: 12

His Xaa Gln Gly Thr Phe Thr Ser Asp Lys Ser Lys Tyr Leu Asp Xaa
1               5                   10                  15
```

-continued

Arg Arg Ala Gln Asp Phe Val Gln Trp Leu Leu Asp Gly Gly Pro Ser
            20                  25                  30

Ser Gly Ala Pro Pro Pro Ser
        35

<210> SEQ ID NO 13
<211> LENGTH: 39
<212> TYPE: PRT
<213> ORGANISM: Artificial
<220> FEATURE:
<223> OTHER INFORMATION: Compound 13
<220> FEATURE:
<221> NAME/KEY: MISC_FEATURE
<222> LOCATION: (2)..(2)
<223> OTHER INFORMATION: X=Aib

<400> SEQUENCE: 13

His Xaa Gln Gly Thr Phe Thr Ser Asp Lys Ser Lys Tyr Leu Asp Glu
1               5                   10                  15

Arg Arg Ala Gln Asp Phe Val Gln Trp Leu Leu Asp Gly Gly Pro Ser
            20                  25                  30

Ser Gly Ala Pro Pro Pro Ser
        35

<210> SEQ ID NO 14
<211> LENGTH: 39
<212> TYPE: PRT
<213> ORGANISM: Artificial
<220> FEATURE:
<223> OTHER INFORMATION: Compound 14
<220> FEATURE:
<221> NAME/KEY: MISC_FEATURE
<222> LOCATION: (2)..(2)
<223> OTHER INFORMATION: X=Aib

<400> SEQUENCE: 14

His Xaa Gln Gly Thr Phe Thr Ser Asp Lys Ser Lys Tyr Leu Asp Glu
1               5                   10                  15

Arg Arg Ala Gln Asp Phe Val Gln Trp Leu Leu Asp Gly Gly Pro Ser
            20                  25                  30

Ser Gly Ala Pro Pro Pro Ser
        35

<210> SEQ ID NO 15
<211> LENGTH: 39
<212> TYPE: PRT
<213> ORGANISM: Artificial
<220> FEATURE:
<223> OTHER INFORMATION: Compound 15
<220> FEATURE:
<221> NAME/KEY: MISC_FEATURE
<222> LOCATION: (2)..(2)
<223> OTHER INFORMATION: X=Aib

<400> SEQUENCE: 15

His Xaa Gln Gly Thr Phe Thr Ser Asp Lys Ser Lys Tyr Leu Asp Glu
1               5                   10                  15

Arg Arg Ala Gln Asp Phe Val Gln Trp Leu Leu Asp Gly Gly Pro Ser
            20                  25                  30

Ser Gly Ala Pro Pro Pro Ser
        35

<210> SEQ ID NO 16
<211> LENGTH: 39
<212> TYPE: PRT

<213> ORGANISM: Artificial
<220> FEATURE:
<223> OTHER INFORMATION: Compound 16
<220> FEATURE:
<221> NAME/KEY: MISC_FEATURE
<222> LOCATION: (2)..(2)
<223> OTHER INFORMATION: X=Aib

<400> SEQUENCE: 16

His Xaa Gln Gly Thr Phe Thr Ser Asp Lys Ser Lys Tyr Leu Asp Glu
1               5                   10                  15

Arg Arg Ala Gln Asp Phe Val Gln Trp Leu Leu Asp Gly Gly Pro Ser
            20                  25                  30

Ser Gly Ala Pro Pro Ser
        35

<210> SEQ ID NO 17
<211> LENGTH: 29
<212> TYPE: PRT
<213> ORGANISM: Artificial
<220> FEATURE:
<223> OTHER INFORMATION: Compound 17
<220> FEATURE:
<221> NAME/KEY: MISC_FEATURE
<222> LOCATION: (2)..(2)
<223> OTHER INFORMATION: D-Ser

<400> SEQUENCE: 17

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Arg Ala
            20                  25

<210> SEQ ID NO 18
<211> LENGTH: 29
<212> TYPE: PRT
<213> ORGANISM: Artificial
<220> FEATURE:
<223> OTHER INFORMATION: Compound 18
<220> FEATURE:
<221> NAME/KEY: MISC_FEATURE
<222> LOCATION: (2)..(2)
<223> OTHER INFORMATION: D-Ser

<400> SEQUENCE: 18

His Ser Gln Gly Thr Phe Thr Ser Asp Tyr Ser Lys Tyr Leu Asp Glu
1               5                   10                  15

Lys Ala Ala Lys Glu Phe Ile Glu Trp Leu Leu Arg Ala
            20                  25

<210> SEQ ID NO 19
<211> LENGTH: 39
<212> TYPE: PRT
<213> ORGANISM: Artificial
<220> FEATURE:
<223> OTHER INFORMATION: Compound 19
<220> FEATURE:
<221> NAME/KEY: MISC_FEATURE
<222> LOCATION: (2)..(2)
<223> OTHER INFORMATION: X=Aib
<220> FEATURE:
<221> NAME/KEY: MISC_FEATURE
<222> LOCATION: (16)..(16)
<223> OTHER INFORMATION: X=Aib

<400> SEQUENCE: 19

His Xaa Gln Gly Thr Phe Thr Ser Asp Lys Ser Lys Tyr Leu Asp Xaa
1               5                   10                  15

Arg Arg Ala Gln Asp Phe Val Gln Trp Leu Leu Asp Gly Gly Pro Ser
            20                  25                  30

Ser Gly Ala Pro Pro Ser
        35

<210> SEQ ID NO 20
<211> LENGTH: 40
<212> TYPE: PRT
<213> ORGANISM: Artificial
<220> FEATURE:
<223> OTHER INFORMATION: Compound 20
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 20

His Ser Gln Gly Thr Phe Thr Ser Asp Tyr Ser Lys Lys Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Ser
        35                  40

<210> SEQ ID NO 21
<211> LENGTH: 39
<212> TYPE: PRT
<213> ORGANISM: Artificial
<220> FEATURE:
<223> OTHER INFORMATION: Compound 21
<220> FEATURE:
<221> NAME/KEY: MISC_FEATURE
<222> LOCATION: (2)..(2)
<223> OTHER INFORMATION: D-Ser

<400> SEQUENCE: 21

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Asn Gly Gly Pro Ser
            20                  25                  30

Ser Gly Ala Pro Pro Ser
        35

<210> SEQ ID NO 22
<211> LENGTH: 39
<212> TYPE: PRT
<213> ORGANISM: Artificial
<220> FEATURE:
<223> OTHER INFORMATION: Compound 22
<220> FEATURE:
<221> NAME/KEY: MISC_FEATURE
<222> LOCATION: (2)..(2)
<223> OTHER INFORMATION: D-Ser

<400> SEQUENCE: 22

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Asn Gly Gly Pro Ser
            20                  25                  30

Ser Gly Ala Pro Pro Ser
        35

```
<210> SEQ ID NO 23
<211> LENGTH: 29
<212> TYPE: PRT
<213> ORGANISM: Artificial
<220> FEATURE:
<223> OTHER INFORMATION: Compound 23
<220> FEATURE:
<221> NAME/KEY: MISC_FEATURE
<222> LOCATION: (2)..(2)
<223> OTHER INFORMATION: D-Ser

<400> SEQUENCE: 23

His Ser Gln Gly Thr Phe Thr Ser Asp Tyr Ser Lys Tyr Leu Asp Glu
1               5                   10                  15

Lys Ala Ala Lys Glu Phe Ile Glu Trp Leu Leu Arg Ala
            20                  25

<210> SEQ ID NO 24
<211> LENGTH: 29
<212> TYPE: PRT
<213> ORGANISM: Artificial
<220> FEATURE:
<223> OTHER INFORMATION: Compound 24
<220> FEATURE:
<221> NAME/KEY: MISC_FEATURE
<222> LOCATION: (2)..(2)
<223> OTHER INFORMATION: D-Ser

<400> SEQUENCE: 24

His Ser Gln Gly Thr Phe Thr Ser Asp Tyr Ser Lys Tyr Leu Asp Glu
1               5                   10                  15

Lys Ala Ala Lys Glu Phe Ile Glu Trp Leu Leu Arg Ala
            20                  25

<210> SEQ ID NO 25
<211> LENGTH: 29
<212> TYPE: PRT
<213> ORGANISM: Artificial
<220> FEATURE:
<223> OTHER INFORMATION: Compound 25
<220> FEATURE:
<221> NAME/KEY: MISC_FEATURE
<222> LOCATION: (2)..(2)
<223> OTHER INFORMATION: D-Ser

<400> SEQUENCE: 25

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Arg Ala
            20                  25

<210> SEQ ID NO 26
<211> LENGTH: 39
<212> TYPE: PRT
<213> ORGANISM: Artificial
<220> FEATURE:
<223> OTHER INFORMATION: Compound 26
<220> FEATURE:
<221> NAME/KEY: MISC_FEATURE
<222> LOCATION: (2)..(2)
<223> OTHER INFORMATION: D-Ser

<400> SEQUENCE: 26

His Ser Gln Gly Thr Phe Thr Ser Asp Tyr Ser Lys Tyr Leu Asp Glu
1               5                   10                  15

Lys Ala Ala Lys Glu Phe Ile Glu Trp Leu Leu Asn Gly Gly Pro Ser
```

Ser Gly Ala Pro Pro Ser
        35

<210> SEQ ID NO 27
<211> LENGTH: 39
<212> TYPE: PRT
<213> ORGANISM: Artificial
<220> FEATURE:
<223> OTHER INFORMATION: Compound 27
<220> FEATURE:
<221> NAME/KEY: MISC_FEATURE
<222> LOCATION: (2)..(2)
<223> OTHER INFORMATION: D-Ser

<400> SEQUENCE: 27

His Ser Gln Gly Thr Phe Thr Ser Asp Tyr Ser Lys Tyr Leu Asp Glu
1               5                   10                  15

Lys Ala Ala Lys Glu Phe Ile Glu Trp Leu Leu Asn Gly Gly Pro Ser
            20                  25                  30

Ser Gly Ala Pro Pro Ser
        35

<210> SEQ ID NO 28
<211> LENGTH: 39
<212> TYPE: PRT
<213> ORGANISM: Artificial
<220> FEATURE:
<223> OTHER INFORMATION: Compound 28
<220> FEATURE:
<221> NAME/KEY: MISC_FEATURE
<222> LOCATION: (2)..(2)
<223> OTHER INFORMATION: D-Ser

<400> SEQUENCE: 28

His Ser Gln Gly Thr Phe Thr Ser Asp Tyr Ser Lys Tyr Leu Asp Glu
1               5                   10                  15

Lys Ala Ala Lys Glu Phe Ile Glu Trp Leu Leu Asn Gly Gly Pro Ser
            20                  25                  30

Ser Gly Ala Pro Pro Ser
        35

<210> SEQ ID NO 29
<211> LENGTH: 39
<212> TYPE: PRT
<213> ORGANISM: Artificial
<220> FEATURE:
<223> OTHER INFORMATION: Compound 29
<220> FEATURE:
<221> NAME/KEY: MISC_FEATURE
<222> LOCATION: (2)..(2)
<223> OTHER INFORMATION: D-Ser

<400> SEQUENCE: 29

His Ser Gln Gly Thr Phe Thr Ser Asp Tyr Ser Lys Tyr Leu Asp Glu
1               5                   10                  15

Lys Ala Ala Lys Glu Phe Ile Glu Trp Leu Leu Asn Gly Gly Pro Ser
            20                  25                  30

Ser Gly Ala Pro Pro Ser
        35

<210> SEQ ID NO 30
<211> LENGTH: 40
<212> TYPE: PRT
<213> ORGANISM: Artificial

-continued

<220> FEATURE:
<223> OTHER INFORMATION: Compound 30
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 30

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 31
<211> LENGTH: 40
<212> TYPE: PRT
<213> ORGANISM: Artificial
<220> FEATURE:
<223> OTHER INFORMATION: Compound 31
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 31

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 32
<211> LENGTH: 40
<212> TYPE: PRT
<213> ORGANISM: Artificial
<220> FEATURE:
<223> OTHER INFORMATION: Compound 32
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 32

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 33
<211> LENGTH: 40

<212> TYPE: PRT
<213> ORGANISM: Artificial
<220> FEATURE:
<223> OTHER INFORMATION: Compound 33
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 33

His Ser Gln Gly Thr Phe Thr Ser Asp Tyr Ser Lys Tyr Leu Asp Xaa
1               5                   10                  15

Lys Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 34
<211> LENGTH: 40
<212> TYPE: PRT
<213> ORGANISM: Artificial
<220> FEATURE:
<223> OTHER INFORMATION: Compound 34
<220> FEATURE:
<221> NAME/KEY: MISC_FEATURE
<222> LOCATION: (2)..(2)
<223> OTHER INFORMATION: D-Ser

<400> SEQUENCE: 34

His Ser Gln Gly Thr Phe Thr Ser Asp Tyr Ser Lys Tyr Leu Asp Lys
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 35
<211> LENGTH: 40
<212> TYPE: PRT
<213> ORGANISM: Artificial
<220> FEATURE:
<223> OTHER INFORMATION: Compound 35
<220> FEATURE:
<221> NAME/KEY: MISC_FEATURE
<222> LOCATION: (2)..(2)
<223> OTHER INFORMATION: D-Ser

<400> SEQUENCE: 35

His Ser Gln Gly Thr Phe Thr Ser Asp Tyr Ser Lys Tyr Leu Asp Lys
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 36
<211> LENGTH: 40
<212> TYPE: PRT
<213> ORGANISM: Artificial
<220> FEATURE:
<223> OTHER INFORMATION: Compound 36
<220> FEATURE:
<221> NAME/KEY: MISC_FEATURE
<222> LOCATION: (2)..(2)
<223> OTHER INFORMATION: D-Ser

<400> SEQUENCE: 36

His Ser Gln Gly Thr Phe Thr Ser Asp Tyr Ser Lys Tyr Leu Asp Lys
1               5                   10                  15

Arg Arg Ala Gln Asp Phe Val Gln Trp Leu Met Asn Thr Gly Gly Pro
            20                  25                  30

Ser Ser Gly Ala Pro Pro Pro Ser
        35                  40

<210> SEQ ID NO 37
<211> LENGTH: 40
<212> TYPE: PRT
<213> ORGANISM: Artificial
<220> FEATURE:
<223> OTHER INFORMATION: Compound 37
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (27)..(27)
<223> OTHER INFORMATION: X=Nle

<400> SEQUENCE: 37

His Ser Gln Gly Thr Phe Thr Ser Asp Tyr Ser Lys Tyr Leu Asp Lys
1               5                   10                  15

Arg Arg Ala Gln Asp Phe Val Gln Trp Leu Xaa Asn Thr Gly Gly Pro
            20                  25                  30

Ser Ser Gly Ala Pro Pro Pro Ser
        35                  40

<210> SEQ ID NO 38
<211> LENGTH: 40
<212> TYPE: PRT
<213> ORGANISM: Artificial
<220> FEATURE:
<223> OTHER INFORMATION: Compound 38
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (27)..(27)
<223> OTHER INFORMATION: X=Nle

<400> SEQUENCE: 38

His Ser Gln Gly Thr Phe Thr Ser Asp Tyr Ser Lys Tyr Leu Asp Lys
1               5                   10                  15

Arg Arg Ala Gln Asp Phe Val Gln Trp Leu Xaa Asn Thr Gly Gly Pro
            20                  25                  30

Ser Ser Gly Ala Pro Pro Pro Ser
        35                  40

<210> SEQ ID NO 39
<211> LENGTH: 40
<212> TYPE: PRT
<213> ORGANISM: Artificial
<220> FEATURE:
<223> OTHER INFORMATION: Compound 39
<220> FEATURE:
<221> NAME/KEY: MISC_FEATURE
<222> LOCATION: (2)..(2)
<223> OTHER INFORMATION: D-Ser -continued

```
<400> SEQUENCE: 39

His Ser Gln Gly Thr Phe Thr Ser Asp Tyr Ser Lys Tyr Leu Asp Lys
1               5                   10                  15

Arg Arg Ala Gln Asp Phe Val Gln Trp Leu Leu Asn Thr Gly Gly Pro
            20                  25                  30

Ser Ser Gly Ala Pro Pro Pro Ser
            35                  40

<210> SEQ ID NO 40
<211> LENGTH: 40
<212> TYPE: PRT
<213> ORGANISM: Artificial
<220> FEATURE:
<223> OTHER INFORMATION: Compound 40
<220> FEATURE:
<221> NAME/KEY: MISC_FEATURE
<222> LOCATION: (2)..(2)
<223> OTHER INFORMATION: D-Ser

<400> SEQUENCE: 40

His Ser Gln Gly Thr Phe Thr Ser Asp Tyr Ser Lys Tyr Leu Asp Lys
1               5                   10                  15

Arg Arg Ala Gln Asp Phe Val Gln Trp Leu Leu Asn Thr Gly Gly Pro
            20                  25                  30

Ser Ser Gly Ala Pro Pro Pro Ser
            35                  40

<210> SEQ ID NO 41
<211> LENGTH: 40
<212> TYPE: PRT
<213> ORGANISM: Artificial
<220> FEATURE:
<223> OTHER INFORMATION: Compound 41
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (27)..(27)
<223> OTHER INFORMATION: X=Nle

<400> SEQUENCE: 41

His Ser Gln Gly Thr Phe Thr Ser Asp Tyr Ser Lys Tyr Leu Asp Lys
1               5                   10                  15

Arg Arg Ala Gln Asp Phe Val Gln Trp Leu Xaa Asn Thr Gly Gly Pro
            20                  25                  30

Ser Ser Gly Ala Pro Pro Pro Ser
            35                  40

<210> SEQ ID NO 42
<211> LENGTH: 40
<212> TYPE: PRT
<213> ORGANISM: Artificial
<220> FEATURE:
<223> OTHER INFORMATION: Compound 42
<220> FEATURE:
<221> NAME/KEY: MISC_FEATURE
<222> LOCATION: (2)..(2)
<223> OTHER INFORMATION: D-Ser

<400> SEQUENCE: 42

His Ser Gln Gly Thr Phe Thr Ser Asp Tyr Ser Lys Tyr Leu Asp Lys
1               5                   10                  15
```

```
Arg Arg Ala Gln Asp Phe Val Gln Trp Leu Leu Asn Thr Gly Gly Pro
            20                  25                  30

Ser Ser Gly Ala Pro Pro Pro Ser
        35                  40

<210> SEQ ID NO 43
<211> LENGTH: 40
<212> TYPE: PRT
<213> ORGANISM: Artificial
<220> FEATURE:
<223> OTHER INFORMATION: Compound 43
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 43

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Leu Asn Thr Gly Gly Pro
            20                  25                  30

Ser Ser Gly Ala Pro Pro Pro Ser
        35                  40

<210> SEQ ID NO 44
<211> LENGTH: 40
<212> TYPE: PRT
<213> ORGANISM: Artificial
<220> FEATURE:
<223> OTHER INFORMATION: Compound 44
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 44

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Leu Asn Thr Gly Gly Pro
            20                  25                  30

Ser Ser Gly Ala Pro Pro Pro Ser
        35                  40

<210> SEQ ID NO 45
<211> LENGTH: 40
<212> TYPE: PRT
<213> ORGANISM: Artificial
<220> FEATURE:
<223> OTHER INFORMATION: Compound 45
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib
<220> FEATURE:
<221> NAME/KEY: MISC_FEATURE
<222> LOCATION: (27)..(27)
<223> OTHER INFORMATION: X=Nle
```

<400> SEQUENCE: 45

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Xaa Asn Thr Gly Gly Pro
            20                  25                  30

Ser Ser Gly Ala Pro Pro Pro Ser
        35                  40

<210> SEQ ID NO 46
<211> LENGTH: 40
<212> TYPE: PRT
<213> ORGANISM: Artificial
<220> FEATURE:
<223> OTHER INFORMATION: Compound 46
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib
<220> FEATURE:
<221> NAME/KEY: MISC_FEATURE
<222> LOCATION: (27)..(27)
<223> OTHER INFORMATION: X=Nle

<400> SEQUENCE: 46

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Xaa Asn Thr Gly Gly Pro
            20                  25                  30

Ser Ser Gly Ala Pro Pro Pro Ser
        35                  40

<210> SEQ ID NO 47
<211> LENGTH: 40
<212> TYPE: PRT
<213> ORGANISM: Artificial
<220> FEATURE:
<223> OTHER INFORMATION: Compound 47
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib

<400> SEQUENCE: 47

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Leu Asn Thr Gly Gly Pro
            20                  25                  30

Ser Ser Gly Ala Pro Pro Pro Ser
        35                  40

<210> SEQ ID NO 48
<211> LENGTH: 40
<212> TYPE: PRT
<213> ORGANISM: Artificial
<220> FEATURE:
<223> OTHER INFORMATION: Compound 48
<220> FEATURE:
<221> NAME/KEY: MISC_FEATURE
<222> LOCATION: (2)..(2)
<223> OTHER INFORMATION: D-Ser
<220> FEATURE:
<221> NAME/KEY: MISC_FEATURE
<222> LOCATION: (16)..(16)
<223> OTHER INFORMATION: X=Aib
<220> FEATURE:
<221> NAME/KEY: MISC_FEATURE
<222> LOCATION: (27)..(27)
<223> OTHER INFORMATION: X=Nle

<400> SEQUENCE: 48

His Ser Gln Gly Thr Phe Thr Ser Asp Lys Ser Lys Tyr Leu Asp Xaa
1               5                   10                  15

Arg Arg Ala Gln Asp Phe Val Gln Trp Leu Xaa Asn Thr Gly Gly Pro
            20                  25                  30

Ser Ser Gly Ala Pro Pro Pro Ser
        35                  40

<210> SEQ ID NO 49
<211> LENGTH: 40
<212> TYPE: PRT
<213> ORGANISM: Artificial
<220> FEATURE:
<223> OTHER INFORMATION: GLP-1R/GCGR Dual Target Agonist Polypeptide
<220> FEATURE:
<221> NAME/KEY: MISC_FEATURE
<222> LOCATION: (2)..(2)
<223> OTHER INFORMATION: X=Aib or D-Ser
<220> FEATURE:
<221> NAME/KEY: MISC_FEATURE
<222> LOCATION: (10)..(10)
<223> OTHER INFORMATION: X=Lys or Tyr
<220> FEATURE:
<221> NAME/KEY: MISC_FEATURE
<222> LOCATION: (13)..(13)
<223> OTHER INFORMATION: X=Lys or Tyr
<220> FEATURE:
<221> NAME/KEY: MISC_FEATURE
<222> LOCATION: (16)..(16)
<223> OTHER INFORMATION: X=Ser, Aib, Lys or Glu
<220> FEATURE:
<221> NAME/KEY: MISC_FEATURE
<222> LOCATION: (17)..(17)
<223> OTHER INFORMATION: X=Lys or Arg
<220> FEATURE:
<221> NAME/KEY: MISC_FEATURE
<222> LOCATION: (18)..(18)
<223> OTHER INFORMATION: Arg or Ala
<220> FEATURE:
<221> NAME/KEY: MISC_FEATURE
<222> LOCATION: (20)..(20)
<223> OTHER INFORMATION: X=His, Gln or Lys
<220> FEATURE:
<221> NAME/KEY: MISC_FEATURE
<222> LOCATION: (21)..(21)
<223> OTHER INFORMATION: X=Asp or Glu
<220> FEATURE:
<221> NAME/KEY: MISC_FEATURE
<222> LOCATION: (23)..(23)
<223> OTHER INFORMATION: X=Ile or Val
<220> FEATURE:
<221> NAME/KEY: MISC_FEATURE
<222> LOCATION: (24)..(24)
<223> OTHER INFORMATION: X=Glu or Gln
<220> FEATURE:
<221> NAME/KEY: MISC_FEATURE
<222> LOCATION: (27)..(27)
<223> OTHER INFORMATION: X=Met, Leu or Nle
<220> FEATURE:
<221> NAME/KEY: MISC_FEATURE
<222> LOCATION: (28)..(28)
<223> OTHER INFORMATION: X=Asn, Asp, Arg, Ser, or is absent
<220> FEATURE:
<221> NAME/KEY: MISC_FEATURE

```
<222> LOCATION: (29)..(29)
<223> OTHER INFORMATION: X=Gly, Thr or is absent
<220> FEATURE:
<221> NAME/KEY: MISC_FEATURE
<222> LOCATION: (30)..(30)
<223> OTHER INFORMATION: X=Gly or is absent
<220> FEATURE:
<221> NAME/KEY: MISC_FEATURE
<222> LOCATION: (31)..(31)
<223> OTHER INFORMATION: X=Gly or is absent
<220> FEATURE:
<221> NAME/KEY: MISC_FEATURE
<222> LOCATION: (32)..(32)
<223> OTHER INFORMATION: X=Pro or is absent
<220> FEATURE:
<221> NAME/KEY: MISC_FEATURE
<222> LOCATION: (33)..(33)
<223> OTHER INFORMATION: X=Ser, Val or is absent
<220> FEATURE:
<221> NAME/KEY: MISC_FEATURE
<222> LOCATION: (34)..(34)
<223> OTHER INFORMATION: X=Ser or is absent
<220> FEATURE:
<221> NAME/KEY: MISC_FEATURE
<222> LOCATION: (35)..(35)
<223> OTHER INFORMATION: X=Gly or is absent
<220> FEATURE:
<221> NAME/KEY: MISC_FEATURE
<222> LOCATION: (36)..(36)
<223> OTHER INFORMATION: X=Ala or is absent
<220> FEATURE:
<221> NAME/KEY: MISC_FEATURE
<222> LOCATION: (37)..(37)
<223> OTHER INFORMATION: X=Pro or is absent
<220> FEATURE:
<221> NAME/KEY: MISC_FEATURE
<222> LOCATION: (38)..(38)
<223> OTHER INFORMATION: X=Pro or is absent
<220> FEATURE:
<221> NAME/KEY: MISC_FEATURE
<222> LOCATION: (39)..(39)
<223> OTHER INFORMATION: X=Pro or is absent
<220> FEATURE:
<221> NAME/KEY: MISC_FEATURE
<222> LOCATION: (40)..(40)
<223> OTHER INFORMATION: X=Ser or is absent

<400> SEQUENCE: 49

His Xaa Gln Gly Thr Phe Thr Ser Asp Xaa Ser Lys Xaa Leu Asp Xaa
 1               5                  10                  15

Xaa Xaa Ala Xaa Xaa Phe Xaa Xaa Trp Leu Xaa Xaa Xaa Xaa Xaa
            20                  25                  30

Xaa Xaa Xaa Xaa Xaa Xaa Xaa Xaa
```

TREATMENT OF BILIARY CIRRHOSIS BASED ON OXYNTOMODULIN ANALOGUE GLP-1R/GCGR DUAL-TARGET AGONIST PEPTIDE

CROSS-REFERENCE

This patent application is section 371 nationalization of PCT Application No. PCT/CN2018/111030 filed Oct. 19, 2018, which claims priority to Chinese Application No. 201711079272.5 filed on Nov. 6, 2017, which applications are incorporated herein by specific reference in their entirety.

FIELD OF THE INVENTION

The present invention belongs to the field of biochemical technology, and specially relates to a GLP-1R/GCGR dual target agonist polypeptide. The present invention also relates to preventive and/or therapeutic uses of the dual target agonist polypeptide for treating diseases such as biliary cirrhosis.

BACKGROUND OF THE INVENTION

In recent years, the number of people died of hepatic cirrhosis all over the world has increased to 0.5 million. The number of people died of hepatic cirrhosis ranks No. five in causes of death in Western Europe, and ranks No. four in America. Hepatic fibrosis is a wound healing response of the liver, representing as hyperplasia and deposition of intrahepatic connective tissue, to hepatic injury caused by various reasons, is an important pathological feature of chronic liver disease, and is also an important link of further improvement to hepatic cirrhosis. Any process damaging environmental stability within the liver, inflammation, toxic damage, hepatic blood flow change, hepatic infection, congenital metabolic disorder, chemical substance and drug toxicity, intrahepatic circulatory disorder and bile flow blockage, congenital anomaly and the like may cause hepatic fibrosis. Wherein, cholestasis is an important factor to cause hepatic fibrosis, and due to denaturation and necrosis of hepatic cells caused by functions of cholic acid and bilirubin and hepatic fibrosis, long-term chronic cholestasis finally leads to hepatic cirrhosis, which is called as biliary cirrhosis in pathology. The cholestasis cirrhosis with known causes is called as Secondary Biliary Cirrhosis (SBC), the intrahepatic cholestasis cirrhosis with unknown causes is called as Primary Biliary Cirrhosis (PBC), and the degree of hepatic fibrosis can have a good prediction to hepatic cirrhosis (Angulo, P. et al. Liver fibrosis, but no other histologic features, is associated with long-term outcomes of patients with nonalcoholic fatty liver disease. *Gastroenterology*, 2015, 149, 389-397.e10.). The principle of bile duct ligation (Liu Ling, Research Status of Animal Models of Bile Duct Ligation (BDL)-Induced Hepatic Fibrosis, *Chongqing Medical Journal*, 2013, 8, 2793-2796.) establishing hepatic fibrosis model is to manually cause extrahepatic biliary obstruction by cutting off the bile duct, resulting in bile duct dilatation and cholestasis above the obstruction portion, an increased pressure within the biliary tract, and causing rupture of intrahepatic bile ductules, such that bilirubin in the bile and a part of bile acid may damage mitochondria, cause disorder of energy generation, free radicals generation, and calcium ions entering into the cell, and lead to dissolution and necrosis of hepatic cells. In addition, since intrahepatic blood vessels suffer from pressure of dilated bile ducts, ischemia and necrosis of hepatic cells also may be caused, finally resulting in hyperplasia of fibrous tissues to extend to bile ducts, encysting hepatic lobule and distributing around hepatic cells to form hepatic fibrosis. Research of Shen, etc. (Shen H, Fan Y, Yang X, et al. Increased expression of cystic fibrosis transmembrance conductance regulator in rat liver after common bile duct ligation. *J Cell Physiol*, 2005, 203, 599-603.) shows that after double ligation at bottom of convergence of hepatic ducts and before convergence of the common bile duct into duodenum, hyperplasia of bile duct cells can be seen for two weeks, hyperplasia of bile duct cells is more obvious for four weeks, accompanying with deformation of hepatic tissue structure, and pseudolobuli within the liver is formed for six weeks. Additional research shows that proliferation of hepatic tissues after BDL is significantly increased, and proliferation after four days of operation reaches a peak, which is twenty-four times of the normal tissue. Similarly, biliary epithelial cells also have proliferation after operation, but such proliferation is temporary, and reaches the maximum after twenty-four hours of the operation, which is fifty times of the normal tissue. After fourty days of BDL, a ratio of hepatic cells is decreased, while a ratio of the bile duct cells and ground substance is increased, an increase of the bile duct ground substance supports new bile duct cells without excessive fibrosis, and such change is closely related to cholestasis time. The absolute number of hepatic cells may be reduced at the stage of cholestasis, because a hepatic volume is increased in the overall stage.

BDL-induced hepatic pathological change is similar with human's biliary cirrhosis, and it is found by Qin Dongmei, etc. (Qin Dongmei, Zhao Wenhui, Hu Liping, etc. Research on Rat Hepatic Fibrosis Model Established by Bile Duct Ligation Operation, *Lishizhen Med Mater Med Res*, 2012, 23, 803-805.) that on the fifth day, fibrous tissues in the portal area and interlobular bile ducts have obvious hyperplasia, blood vessels around central veins have dilatation and congestion, and inflammatory cell infiltration also has occurred around mesenchyme through bile duct ligation replication models of sixty Wistar rats using HE dye. The establishing time of the model is relatively short, experimenters and animals do not contact toxic substance, and fibrosis is rapidly formed with a low spontaneous reversal rate and a good stability. Kazuyoshi, etc. (Kazuyoshi T, Yuko K, Kenichi I K, et al. Death receptor 5 mediated-apoptosis contributes to cholestasis liver disease. *PNAS*, 2008, 10895-10900.) researched the function of TRAIL/DR5 mediated signal channel in the course of biliary hepatic diseases with BDL models of mice. Moreover, rats have an abundant source, a low cost and a small size for convenient transportation, and easier batch feeding, and are the common experimental animals for establishing model of hepatic fibrosis.

Obeticholic Acid (product name: Ocaliva) is the second drug approved for treating patients with Primary Biliary Cirrhosis (PBC) within twenty years after ursodeoxycholic acid (UDCA) approved as orphan drug, and is approved for treating adult patients with PBC in poor response to UDCA monotherapy, or adult patients with PBC being intolerant monotherapy, associating with UDCA by FDA on May 31, 2016. In addition, as for the effective amount of Obeticholic Acid, it is still to be evaluated (Liu Songtao, Liao Huiyu. Clinical Study and Progress of Obeticholic Acid, *Beijing Medical Journal*, 2015, 37, 1174-1176). Currently, adverse reactions of Obeticholic Acid become the highly focused issue. The most common adverse reactions are pruritus, an increase of low density lipoprotein and a decrease of high-density lipoprotein (Kowdley K V, Jones D, Luketic V, et al. An international study evaluating the farnesoid X receptor agonist obeticholic acid as monotherapy in PBC. *J. Hepatol*, 2011, 54, 13.). It is reported in the documents that an occurrence rate of pruritus reaches 30% to 94%, and has a tendency of rise as the amount is increased. A part of patients discontinue the drug due to severe pruritus.

Till now, there is no specific therapeutic drug for treating PBC patient. In recent years, exploration of drugs for treatment of diseases such as biliary cirrhosis attracts more and more attention, and researchers relieve or treat the course of biliary cirrhosis by trying drug synthesis at different links and functional health. However, currently, only Obeticholic Acid approved on the market has a significant improvement for therapy of a part of patients. Although some cytokine preparations have a certain therapeutic effect on therapy of biliary cirrhosis, none can be applied to clinic treatment till now. Therefore, active development of new drugs for prevention and treatment of biliary cirrhosis is a hot spot in current medical research work.

SUMMARY OF THE INVENTION

In the Chinese patent No. ZL 201510237027.7 found by the inventor, by molecule modification of oxyntomudulin (OXM), has obtained a kind of GLP-1R/GCGR dual target agonists as oxyntomudulin analogues having a longer half-life and insulinotropic activity without adverse events. The GLP-1R/GCGR dual target agonists can be used for treatment of diseases such as diabetes. Further experiments are carried out for the present invention, and new biological activity of such GLP-1R/GCGR dual target agonist polypeptides and their therapeutic uses and indications are provided.

The object of the invention is to provide biological activity and therapeutic uses of such GLP-1R/GCGR dual target agonist polypeptides in inhibition and improvement of biliary cirrhosis and related hepatic fibrosis course.

The inventor has demonstrated that such GLP-1R/GCGR dual target agonist polypeptides can significantly inhibit activation of human hepatic stellate cells (LX-2) in vitro through a great number of experimental studies, suggesting that active polypeptides have excellent in vitro anti-hepatic fibrosis effect. Meanwhile, such polypeptides can significantly improve a degree of BDL-induced cholestasis hepatic fibrosis in rats. It is proved that such GLP-1R/GCGR dual target agonist polypeptides have significant therapeutic effects on diseases such as biliary cirrhosis.

Another object of the invention is to provide new therapeutic uses of such GLP-1R/GCGR dual target agonist polypeptides for indications. Such GLP-1R/GCGR dual target agonist polypeptides are expected to be new generation of preventive or therapeutic drugs for biliary cirrhosis and related hepatic fibrosis diseases.

The invention relates to GLP-1R/GCGR dual target agonist polypeptides comprising the parent peptide represented by the following amino acid sequence: His-Xaa2-Gln-Gly-Thr-Phe-Thr-Ser-Asp-Xaa10-Ser-Lys-Xaa13-Leu-Asp-Xaa16-Xaa17-Xaa18-Ala-Xaa20-Xaa21-Phe-Xaa23-Xaa24-Trp-Leu-Xaa27-Xaa28-Xaa29-Xaa30-Xaa31-Xaa32-Xaa33-Xaa34-Xaa35-Xaa36-Xaa37-Xaa38-Xaa39-Xaa40-COR$_1$ (SEQ ID NO: 49)

wherein, R$_1$=—NH$_2$;
Xaa2=Aib or D-Ser;
Xaa10=Lys or Tyr;
Xaa13=Lys or Tyr;
Xaa16=Ser, Aib, Lys or Glu;
Xaa17=Lys or Arg;
Xaa18=Arg or Ala;
Xaa20=His, Gln or Lys;
Xaa21=Asp or Glu;
Xaa23=Ile or Val;
Xaa24=Glu or Gln;
Xaa27=Met, Leu or Nle;
Xaa28=Asn, Asp, Arg, Ser or is absent;
Xaa29=Gly, Thr or is absent;
Xaa30=Gly or is absent;
Xaa31=Gly or is absent;
Xaa32=Pro or is absent;
Xaa33=Ser, Val or is absent;
Xaa34=Ser or is absent;
Xaa35=Gly or is absent;
Xaa36=Ala or is absent;
Xaa37=Pro or is absent;
Xaa38=Pro or is absent;
Xaa39=Pro or is absent;
Xaa40=Ser or is absent.

In the amino acid sequence, at least one of Xaa10, Xaa16, Xaa17 or Xaa20 is Lys, the side chain of the at least one Lys or the Lys at position 12 is attached to a lipophilic substituent in such a way that a carboxyl group of the lipophilic substituent forms an amide bond with an amino group of a bridging group, the bridging group is attached to the parent peptide by means of a carboxyl group of the amino acid residue of the bridging group which forms an amide bond with the amino group of the side chain of said at least one Lys or the Lys of the parent peptide. The bridging group is Glu, Asp, and/or (PEG)m, wherein m is an integer of 2-10; and the lipophilic substituent is an acyl group selected from CH$_3$(CH$_2$)$_n$CO— or HOOC(CH$_2$)$_n$CO—, wherein n is an integer of 10-24. The preferred bridging group may be Glu-(PEG)$_m$ or Asp-(PEG)$_m$ or (PEG)$_m$, which is attached in the way as follows:

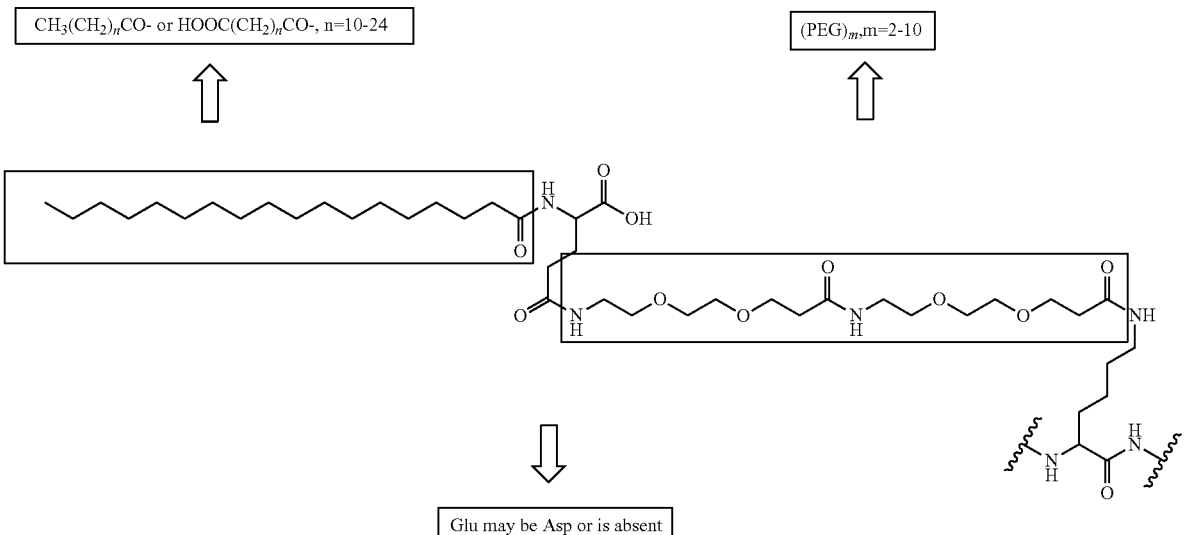

The compounds of the invention are based on the theory that the intramolecular bridges can stabilize the helical structure of the molecule and so increase potency and/or selectivity at the GLP-1R or GCGR receptors. The compounds of the invention carry one or more intramolecular bridges within the sequence. Each such bridge is formed between the side chains of two amino acid residues which are typically separated by three amino acids in the linear sequence. For example, the bridge may be formed between the side chains of residue pairs 12 and 16, 16 and 20, 17 and 21, or 20 and 24. The two side chains can be linked to one another through ionic interactions, or by covalent bonds. Thus these pairs of residues may comprise oppositely charged side chains in order to form a salt bridge by ionic interactions. For example, one of the residues may be Glu or Asp, while the other residue may be Lys or Arg. The pairings of Lys and Glu as well as Lys and Asp may also be capable of reacting to form a lactam ring respectively.

The invention is also to provide a pharmaceutical composition comprising the GLP-1R/GCGR dual target agonist polypeptides of the invention. The pharmaceutical composition is prepared using the GLP-1R/GCGR dual target agonist polypeptides as an active ingredient added with pharmaceutically acceptable carriers and/or excipients.

The polypeptides of the invention are effective in improvement and treatment of biliary cirrhosis and related hepatic fibrosis diseases. The polypeptides of the invention can be used for direct or indirect therapy of any condition caused or characterized by biliary cirrhosis and related hepatic fibrosis course.

The person skilled in the art can appreciate that the pharmaceutical composition of the invention is suitable for various administration routes, such as oral administration, percutaneous administration, intravenous administration, intramuscular administration, topical administration and intranasal administration. According to the used administration route, the pharmaceutical composition of the invention can be formulated into various suitable dosage forms, which comprises an effective amount of at least one polypeptide of the invention and at least one pharmaceutically acceptable pharmaceutical carrier.

Examples of suitable dosage forms are tablets, capsules, sugar coated tablets, granules, oral liquid and syrup, ointment and paste for the skin surface, aerosol, nasal spray and sterile solution for injection.

The pharmaceutical composition comprising the polypeptides of the invention may be prepared into solution or lyophilized powder for parenteral administration. Before use, an appropriate solvent or other pharmaceutically acceptable carrier can be added to reconfigure the powder, and liquid formula is generally buffer, osmotic solution and aqueous solution.

The dosage of the polypeptides of the invention in the pharmaceutical composition may vary in a wide range, which can be easily determined by the person skilled in this art according to certain factors such as the type of the disease, the severity of the disease, patient's body weight, the dosage form and the administration route.

The invention has the advantages of:
1) having outstanding biological activity;
2) showing stability in pharmacokinetics experiment of the drug, having good stability, ease to be produced on large scale, and low cost;
3) having lower toxicity, larger safety window and smaller amount compared with small molecule compounds.

In particular embodiments, the following GLP-1R/GCGR dual target agonist polypeptides are related, having the following sequences:

Compound 1 (SEQ ID NO: 1):
His-(D-Ser)-Gln-Gly-Thr-Phe-Thr-Ser-Asp-Tyr-Ser-Lys(PEG$_2$-PEG2-γGlu-CO(CH$_2$)$_{14}$CH$_3$)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSDYS-K(PEG$_2$-PEG$_2$-γGlu-CO(CH$_2$)$_{14}$CH$_3$)-KLD-Aib-RRAQDFVQWLMNTGGPSSGAPPPS-NH$_2$ Compound 2 (SEQ ID NO: 2):
His-(D-Ser)-Gln-Gly-Thr-Phe-Thr-Ser-Asp-Tyr-Ser-Lys(PEG$_2$-PEG$_2$-CO(CH$_2$)$_{16}$CO$_2$H)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSDYS-K(PEG$_2$-PEG$_2$-CO(CH$_2$)$_{16}$CO$_2$H)KLD-Aib-RRAQDFVQWLMNTGGPSSGAPPPS-NH$_2$ Compound 3 (SEQ ID NO: 3):
His-(D-Ser)-Gln-Gly-Thr-Phe-Thr-Ser-Asp-Tyr-Ser-Lys(PEG$_2$-PEG$_2$-CO(CH$_2$)$_{16}$CH$_3$)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ H-(d-S)-QGTFTSDYS-K(PEG$_2$-PEG$_2$-CO(CH$_2$)$_{16}$CH$_3$)-KLD-Arib-RRAQDFVQWLMNTGGPSSGAPPPS-NH$_2$ Compound 4 (SEQ ID NO: 4):
His-(D-Ser)-Gln-Gly-Thr-Phe-Thr-Ser-Asp-Lys(PEG)-PEG$_2$-γGlu-CO(CH$_2$)$_{14}$CH$_3$)-Ser-Lys-Tyr-Leu-Asp-Aib-Arg-Arg-Ala-Gln-Asp-Phe-Val-Gln-Trp-Leu-Met- Asn-Thr-Gly-Gly-Pro-Ser-Ser-Gly-Ala-Pro-Pro-Pro-Ser-NH$_2$ H-(d-S)-QGTFTSD-K(PEG$_2$-PEG$_2$-γGlu-CO(CH$_2$)$_{14}$CH$_3$)-SKYLD-Aib-RRAQD

FVQWLMNTGGPSSGAPPPS

Compound 5 (SEQ ID NO: 5):
His-(D-Ser)-Gln-Gly-Thr-Phe-Thr-Ser-Asp-Lys(PEG)-PEG$_2$-γGlu-CO(CH$_2$)$_{16}$ CO$_2$H)-Ser-Lys-Tyr-Leu-Asp-Aib-Arg-Arg-Ala-Gln-Asp-Phe-Val-Gln-Trp-Leu- Met-Asn-Thr-Gly-Gly-Pro-Ser-Ser-Gly-Ala-Pro-Pro-Pro-Ser-NH$_2$ H-(d-S)-QGTFTSD-K(PEG$_2$-PEG$_2$-γGlu-CO(CH$_2$)$_{16}$CO$_2$H)-SKYTD-Aib-RRAQ

DFVQWLMNTGGPSSGAPPPS-NH$_2$

Compound 6 (SEQ ID NO: 6):
His-(D-Ser)-Gln-Gly-Thr-Phe-Thr-Ser-Asp-Tyr-Ser-Lys-Tyr-Leu-Asp-Lys(PEG$_2$-

PEG$_2$-γGlu-CO(CH$_2$)$_{14}$CH$_3$)-Arg-Arg-Ala-Gln-Asp-Phe-Val-Gln-Trp-Leu-Met-Asn-

Thr-Gly-Gly-Pro-Ser-Ser-Gly-Ala-Pro-Pro-Pro-Ser-NH$_2$

H-(d-S)-QGTFTSDYSKYLD-K(PEG$_2$-PEG$_2$-γGlu-CO(CH$_2$)$_{14}$CH$_3$)-RRAQDFV

QWLMNTGGPSSGAPPPS-NH$_2$

Compound 7 (SEQ ID NO: 7):
His-(D-Ser)-Gln-Gly-Thr-Phe-Thr-Ser-Asp-Tyr-Ser-Lys-Tyr-Leu-Asp-Aib-Lys (PEG$_2$-PEG$_2$-γGlu-CO(CH$_2$)$_{16}$CO$_2$H)-Arg-Ala-Gln-Asp-Phe-Val-Gln-Trp-Leu-Met- Asn-Thr-Gly-Gly-Pro-Ser-Ser-Gly-Ala-Pro-Pro-Pro-Ser-NH$_2$ H-(d-S)-QGTFTSDYSKYLD-Aib-K(PEG$_2$-PEG$_2$-γGlu-CO(CH$_2$)$_{16}$CO$_2$H)-RAQD

FVQWLMNTGGPSSGAPPPS-NH$_2$

Compound 8 (SEQ ID NO: 8):
His-Aib-Gln-Gly-Thr-Phe-Thr-Ser-Asp-Lys(PEG$_2$-PEG$_2$-γGlu-CO(CH$_2$)$_{14}$CH$_3$)-

Ser-Lys-Tyr-Leu-Asp-Aib-Arg-Arg-Ala-Gln-Asp-Phe-Val-Gln-Trp-Leu-Leu-Asp-

Gly-Gly-Pro-Ser-Ser-Gly-Ala-Pro-Pro-Pro-Ser-NH$_2$

H-Aib-QGTFTSD-K(PEG$_2$-PEG$_2$-γGlu-CO(CH$_2$)$_{14}$CH$_3$)-SKYLD-Aib-RRAQDF

VQWLLDGGPSSGAPPPS-NH$_2$

Compound 9 (SEQ ID NO: 9):
His-(D-Ser)-Gln-Gly-Thr-Phe-Thr-Ser-Asp-Tyr-Ser-Lys(PEG$_2$-PEG$_2$-CO(CH2)$_{14}$ CH$_3$)-Lys-Leu-Asp-Aib-Arg-Arg-Ala-Gln-Asp-Phe-Val-Gln-Trp-Leu-Met-Asn- Thr-Gly-Gly-Pro-Ser-Ser-Gly-Ala-Pro-Pro-Pro-Ser-NH$_2$ H-(d-S)-QGTFTSDYS-K(PEG$_2$-PEG$_2$-CO(CH$_2$)$_{14}$CH$_3$)-SKYLD-Aib-RRAQDFVQ

WLMNTGGPSSGAPPPS-NH$_2$

Compound 10 (SEQ ID NO: 10):
His-(D-Ser)-Gln-Gly-Thr-Phe-Thr-Ser-Asp-Tyr-Ser-Lys-Tyr-Leu-Asp-Aib-Lys (PEG$_2$-PEG$_2$-CO(CH$_2$)$_{16}$CO$_2$H)-Arg-Ala-Gln-Asp-Phe-Val-Gln-Trp-Leu-Met-Asn- Thr-Gly-Gly-Pro-Ser-Ser-Gly-Ala-Pro-Pro-Pro-Ser-NH$_2$ H-(d-S)-QGTFTSDYSKYLD-Aib-K(PEG$_2$-PEG$_2$-CO(CH$_2$)$_{16}$CO$_2$H)-RAQDFVQ

WLMNTGGPSSGAPPPS-NH$_2$

Compound 11 (SEQ ID NO: 11):
His-Aib-Gln-Gly-Thr-Phe-Thr-Ser-Asp-Lys(PEG$_2$-PEG$_2$-γGlu-CO(CH$_2$)$_{14}$CO$_2$H)-

Ser-Lys-Tyr-Leu-Asp-Aib-Arg-Arg-Ala-Gln-Asp-Phe-Val-Gln-Trp-Leu-Leu-Asp-

Gly-Gly-Pro-Ser-Ser-Gly-Ala-Pro-Pro-Pro-Ser-NH$_2$

-continued

H-Aib-QGTFTSD-K(PEG$_2$-PEG$_2$-γGlu-CO(CH$_2$)$_{14}$CO$_2$H)-SKYLD-Aib-RRAQD

FVQWLLDGGPSSGAPPPS-NH$_2$

Compound 12 (SEQ ID NO: 12):
His-Aib-Gln-Gly-Thr-Phe-Thr-Ser-Asp-Lys(PEG$_2$-PEG$_2$-γGlu-CO(CH$_2$)$_{16}$CH$_3$)-

Ser-Lys-Tyr-Leu-Asp-Aib-Arg-Arg-Ala-Gln-Asp-Phe-Val-Gln-Trp-Leu-Leu-Asp-

Gly-Gly-Pro-Ser-Ser-Gly-Ala-Pro-Pro-Pro-Ser-NH$_2$

H-Aib-QGTFTSD-K(PEG$_2$-PEG$_2$-γGlu-CO(CH$_2$)$_{16}$CH$_3$)-SKYLD-Aib-RRAQDF

VQWLLDGGPSSGAPPPS-NH$_2$

Compound 13 (SEQ ID NO: 13):
His-Aib-Gln-Gly-Thr-Phe-Thr-Ser-Asp-Lys(PEG$_2$-PEG$_2$-γGlu-CO(CH$_2$)$_{14}$CO$_2$H)-

Ser-Lys-Tyr-Leu-Asp-Glu-Arg-Arg-Ala-Gln-Asp-Phe-Val-Gln-Trp-Leu-Leu-Asp-

Gly-Gly-Pro-Ser-Ser-Gly-Ala-Pro-Pro-Pro-Ser-NH$_2$

H-Aib-QGTFTSD-K(PEG$_2$-PEG$_2$-γGlu-CO(CH$_2$)$_{14}$CO$_2$H-SYLDERRAQDFV

QWLLDGGPSSGAPPPS-NH$_2$

Compound 14 (SEQ ID NO: 14):
His-Aib-Gln-Gly-Thr-Phe-Thr-Ser-Asp-Lys(PEG$_2$-PEG$_2$-γGlu-CO(CH$_2$)$_{16}$CH$_3$)-

Ser-Lys-Tyr-Leu-Asp-Glu-Arg-Arg-Ala-Gln-Asp-Phe-Val-Gln-Trp-Leu-Leu-Asp-

Gly-Gly-Pro-Ser-Ser-Gly-Ala-Pro-Pro-Pro-Ser-NH$_2$

H-Aib-QGTFTSD-K(PEG$_2$-PEG$_2$-γGlu-CO(CH$_2$)$_{16}$CH$_3$)-SKYLDERRAQDFVQ

WLLDGGPSSGAPPPS-NH$_2$

Compound 15 (SEQ ID NO: 15):
His-Aib-Gln-Gly-Thr-Phe-Thr-Ser-Asp-Lys(PEG$_2$-PEG$_2$-γGlu-CO(CH$_2$)$_{16}$CO$_2$H)-

Ser-Lys-Tyr-Leu-Asp-Glu-Arg-Arg-Ala-Gln-Asp-Phe-Val-Gln-Trp-Leu-Leu-Asp-

Gly-Gly-Pro-Ser-Ser-Gly-Ala-Pro-Pro-Pro-Ser-NH$_2$

H-Aib-QGTFTSD-K(PEG$_2$-PEG$_2$-γGln-CO(CH$_2$)$_{16}$CO$_2$H)-SKYLDERRAQDFN

QWLLDGGPSSGAPPPS-NH$_2$

Compound 16 (SEQ ID NO: 16):
His-Aib-Gln-Gly-Thr-Phe-Thr-Ser-Asp-Lys(PEG$_2$-PEG$_2$-γGlu-CO(CH$_2$)$_{14}$CH$_3$)-

Ser-Lys-Tyr-Leu-Asp-Glu-Arg-Arg-Ala-Gln-Asp-Phe-Val-Gln-Trp-Leu-Leu-Asp-

Gly-Gly-Pro-Ser-Ser-Gly-Ala-Pro-Pro-Pro-Ser-NH$_2$

H-Aib-QGTFTSD-K(PEG$_2$-PEG$_2$-γGlu-CO(CH$_2$)$_{14}$CH$_3$)-SKYLDERRAQDFVQ

WLLDGGPSSGAPPPS-NH$_2$

Compound 17 (SEQ ID NO: 17):
His-(D-Ser)-Gln-Gly-Thr-Phe-Thr-Ser-Asp-Tyr-Ser-Lys-Tyr-Leu-Asp-Ser-Lys (PEG$_2$-PEG$_2$-γGlu-CO(CH$_2$)$_{16}$CO$_2$H)-Ala-Ala-His-Asp-Phe-Val-Glu-Trp-Leu-Leu- Arg-Ala-NH$_2$ H-(d-S)-QGTFTSDYSKYLDS-K(PEG$_2$-PEG$_2$-γGlu-CO(CH$_2$)$_{16}$CO$_2$H)-AAHDEV

EWLLRA-NH$_2$

Compound 18 (SEQ ID NO: 18):
His-(D-Ser)-Gln-Gly-Thr-Phe-Thr-Ser-Asp-Tyr-Ser-Lys-Tyr-Leu-Asp-Glu-Lys- Ala-Ala-Lys(PEG$_2$-PEG$_2$-γGlu-CO(CH$_2$)$_{16}$CO$_2$H)-Glu-Phe-Ile-Glu-Trp-Leu-Leu- Arg-Ala-NH$_2$ H-(d-S)-QGTFTSDYSKYLDEKAA-K(PEG$_2$-PEG$_2$-γGlu-CO(CH$_2$)$_{16}$CO$_2$H)-EFI

EWLLRA-NH$_2$

-continued

Compound 19 (SEQ ID NO: 19):
His-Aib-Gln-Gly-Thr-Phe-Thr-Ser-Asp-Lys(PEG$_2$-PEG$_2$-γGlu-CO(CH$_2$)$_{16}$CO$_2$H)-
Ser-Lys-Tyr-Leu-Asp-Aib-Arg-Arg-Ala-Gln-Asp-Phe-Val-Gln-Trp-Leu-Leu-Asp-
Gly-Gly-Pro-Ser-Ser-Gly-Ala-Pro-Pro-Pro-Ser-NH$_2$ H-Aib-QGTFTSD-K(PEG$_2$-PEG$_2$-γGlu-CO(CH$_2$)$_{16}$CO$_2$H)-SKYLD-Aib-RRAQD
FVQWLLDGGPSSGAPPPS-NH$_2$ Compound 20 (SEQ ID NO: 20):
His-(D-Ser)-Gln-Gly-Thr-Phe-Thr-Ser-Asp-Tyr-Ser-Lys(PEG$_2$-PEG$_2$-γGlu-CO
(CH$_2$)$_{16}$CO$_2$H)-Lys-Leu-Asp-Aib-Arg-Arg-Ala-Gln-Asp-Phe-Val-Gln-Trp-Leu-Met-
Asn-Thr-Gly-Gly-Pro-Ser-Ser-Gly-Ala-Pro-Pro-Pro-Ser-NH$_2$ H-(d-S)-QGTFTSDYS-K(PEG$_2$-PEG$_2$-γGlu-CO(CH$_2$)$_{16}$CO$_2$H)-KLD-Aib-RRAQ
DFVQWLMNTGGPSSGAPPPS-NH$_2$ Compound 21 (SEQ ID NO: 21):
His-(D-Ser)-Gln-Gly-Thr-Phe-Thr-Ser-Asp-Tyr-Ser-Lys-Tyr-Leu-Asp-Ser-Lys
(PEG$_2$-PEG$_2$-γGlu-CO(CH$_2$)$_{16}$CO$_2$H)-Ala-Ala-His-Asp-Phe-Val-Glu-Trp-Leu-Leu-
Asn-Gly-Gly-Pro-Ser-Ser-Gly-Ala-Pro-Pro-Pro-Ser-NH$_2$ H-(d-S)-QGTFTSDYSKYLDS-K(PEG$_2$-PEG$_2$-γGlu-CO(CH$_2$)$_{16}$CO$_2$H)-AAHDFV
EWLLNGGPSSGAPPPS-NH$_2$ Compound 22 (SEQ ID NO: 22):
His-(D-Ser)-Gln-Gly-Thr-Phe-Thr-Ser-Asp-Tyr-Ser-Lys-Tyr-Leu-Asp-Ser-Lys
(PEG$_2$-PEG$_2$-γGlu-CO(CH$_2$)$_{16}$CH$_3$)-Ala-Ala-His-Asp-Phe-Val-Glu-Trp-Leu-Leu-
Asn-Gly-Gly-Pro-Ser-Ser-Gly-Aln-Pro-Pro-Pro-Ser-NH$_2$ H-(d-S)-QGTFTSDYSKYLDS-K(PEG$_2$-PEG$_2$-γGlu-CO(CH$_2$)$_{16}$CH$_3$)-AAHDFVE
WLLNGGPSSGAPPPS-NH$_2$ Compound 23 (SEQ ID NO: 23):
His-(D-Ser)-Gln-Gly-Thr-Phe-Thr-Ser-Asp-Tyr-Ser-Lys-Tyr-Leu-Asp-Glu-Lys-
Ala-Ala-Lys(PEG$_2$-PEG$_2$-γGlu-CO(CH$_2$)$_{14}$CH$_3$)-Glu-Phe-Ile-Glu-Trp-Leu-Leu-Arg-
Ala-NH$_2$ H-(d-S)-QGTFTSDYSKYLDEKAA-K(PEG$_2$-PEG$_2$-γGlu-CO(CH$_2$)$_{14}$CH$_3$)-EFIE
WLLRA-NH$_2$ Compound 24 (SEQ ID NO: 24):
His-(D-Ser)-Gln-Gly-Thr-Phe-Thr-Ser-Asp-Tyr-Ser-Lys-Tyr-Leu-Asp-Glu-Lys-
Ala-Ala-Lys(PEG$_2$-PEG$_2$-γGlu-CO(CH$_2$)$_{16}$CH$_3$)-Glu-Phe-Ile-Glu-Trp-Leu-Leu-Arg-
Ala-NH$_2$ H-(d-S)-QGTFTSDYSKYLDEKAA-K(PEG$_2$-PEG$_2$-γGlu-CO(CH$_2$)$_{16}$CH$_3$-EFIE
WLLRA-NH$_2$ Compound 25 (SEQ ID NO: 25):
His-(D-Ser)-Gln-Gly-Thr-Phe-Thr-Ser-Asp-Tyr-Ser-Lys-Tyr-Leu-Asp-Ser-Lys
(PEG$_2$-PEG$_2$-γGlu-CO(CH$_2$)$_{16}$CH$_3$)-Ala-Ala-His-Asp-Phe-Val-Glu-Trp-Leu-Leu-Arg-
Ala-NH$_2$ H-(d-S)-QGTFTSDYSKYLDS-K(PEG$_2$-PEG$_2$-γGlu-CO(CH$_2$)$_{16}$CH$_3$)-AAHDFVE
WLLRA-NH$_2$ Compound 26 (SEQ ID NO: 26):
His-(D-Ser)-Gln-Gly-Thr-Phe-Thr-Ser-Asp-Tyr-Ser-Lys-Tyr-Leu-Asp-Glu-Lys-
Ala-Ala-Lys(PEG$_2$-PEG$_2$-γGlu-CO(CH$_2$)$_{16}$CO$_2$H)-Glu-Phe-Ile-Glu-Trp-Leu-Leu- Asn-Gly-Gly-Pro-Ser-Ser-Gly-Ala-Pro-Pro-Pro-Ser-NH$_2$ H-(d-S)-QGTFTSDYSKYLDEKAA-K(PEG$_2$-PEG$_2$-γGlu-CO(CH$_2$)$_{16}$CO$_2$H)-EFI

EWLLNGGPSSGAPPPS-NH$_2$

Compound 27 (SEQ ID NO: 27):
His-(D-Ser)-Gln-Gly-Thr-Phe-Thr-Ser-Asp-Tyr-Ser-Lys-Tyr-Leu-Asp-Glu-Lys- Ala-Ala-Lys(PEG$_2$-PEG$_2$-γGlu-CO(CH$_2$)$_{14}$CO$_2$H)-Glu-Phe-Ile-Glu-Trp-Leu-Leu- Asn-Gly-Gly-Pro-Ser-Ser-Gly-Ala-Pro-Pro-Pro-Ser-NH$_2$ H-(d-S)-QGTFTSDYSKYLDEKAA-K(PEG$_2$-PEG$_2$-γGlu-CO(CH$_2$)$_{14}$CO$_2$H)-EFI

EWLLNGGPSSGAPPPS-NH$_2$

Compound 28 (SEQ ID NO: 28):
His-(D-Ser)-Gln-Gly-Thr-Phe-Thr-Ser-Asp-Tyr-Ser-Lys-Tyr-Leu-Asp-Glu-Lys- Ala-Ala-Lys(PEG$_2$-PEG$_2$-γGlu-CO(CH$_2$)$_{16}$CH$_3$)-Glu-Phe-Ile-Glu-Trp-Leu-Leu-Asn- Gly-Gly-Pro-Ser-Ser-Gly-Ala-Pro-Pro-Pro-Ser-NH$_2$ H-(d-S)-QGTFTSDYSKYLDEKAA-K(PEG$_2$-PEG$_2$-γGlu-CO(CH$_2$)$_{16}$CH$_3$)-EFIE

WLLNGGPSSGAPPPS-NH$_2$

Compound 29 (SEQ ID NO: 29):
His-(D-Ser)-Gln-Gly-Thr-Phe-Thr-Ser-Asp-Tyr-Ser-Lys-Tyr-Leu-Asp-Glu-Lys- Ala-Ala-Lys(PEG$_2$-PEG$_2$-γGlu-CO(CH$_2$)$_{14}$CH$_3$)-Glu-Phe-Ile-Glu-Trp-Leu-Leu-Asn- Gly-Gly-Pro-Ser-Ser-Gly-Ala-Pro-Pro-Pro-Ser-NH$_2$ H-(d-S)-QGTFTSDYSKYLDEKAA-K(PEG$_2$-PEG$_2$-γGlu-CO(CH$_2$)$_{14}$CH$_3$)-EFIE

WLLNGGPSSGAPPPS-NH$_2$

Compound 30 (SEQ ID NO: 30):
His-(D-Ser)-Gln-Gly-Thr-Phe-Thr-Ser-Asp-Lys(PEG$_2$-PEG$_2$-CO(CH$_2$)$_{16}$CO$_2$H)-

Ser-Lys-Tyr-Leu-Asp-Aib-Arg-Arg-Ala-Gln-Asp-Phe-Val-Gln-Trp-Leu-Met-

Asn-Thr-Gly-Gly-Pro-Ser-Ser-Gly-Ala-Pro-Pro-Pro-Ser-NH$_2$

H-(d-S)-QGTFTSD-K(PEG$_2$-PEG$_2$-CO(CH$_2$)$_{16}$CO$_2$H)-SKYLD-Aib-RRAQDFVQ

WLMNTGGPSSGAPPPS-NH$_2$

Compound 31 (SEQ ID NO: 31):
His-(D-Ser)-Gln-Gly-Thr-Phe-Thr-Ser-Asp-Lys(PEG$_2$-PEG$_2$-CO(CH$_2$)$_{14}$CH$_3$)-

Ser-Lys-Tyr-Leu-Asp-Aib-Arg-Arg-Ala-Gln-Asp-Phe-Val-Gln-Trp-Leu-Met-

Asn-Thr-Gly-Gly-Pro-Ser-Ser-Gly-Ala-Pro-Pro-Pro-Ser-NH$_2$

H-(d-S)-QGTFTSD-K(PEG$_2$-PEG$_2$-CO(CH$_2$)$_{14}$CH$_3$)-SKYLD-Aib-RRAQDFVQ

WLMNTGGPSSGAPPPS-NH$_2$

Compound 32 (SEQ ID NO: 32):
His-(D-Ser)-Gln-Gly-Thr-Phe-Thr-Ser-Asp-Lys(PEG$_2$-PEG$_2$-CO(CH$_2$)$_{16}$CH$_3$)-

Ser-Lys-Tyr-Leu-Asp-Aib-Arg-Arg-Ala-Gln-Asp-Phe-Val-Gln-Trp-Leu-

Met-Asn-Thr-Gly-Gly-Pro-Ser-Ser-Gly-Ala-Pro-Pro-Pro-Ser-NH$_2$

H-(d-S)-QGTFTSD-K(PEG2-PEG$_2$-CO(CH$_2$)$_{14}$CH$_3$)-SKYLD-Aib-RRAQDFVQ

WLMNTGGPSSGAPPPS-NH$_2$

Compound 33 (SEQ ID NO: 33):
His-(D-Ser)-Gln-Gly-Thr-Phe-Thr-Ser-Asp-Tyr-Ser-Lys-Tyr-Leu-Asp-Aib-Lys (PEG$_2$-PEG$_2$-γGlu-CO(CH$_2$)$_{14}$CH$_3$)-Arg-Ala-Gln-Asp-Phe-Val-Gln-Trp-Leu-Met- Asn-Thr-Gly-Gly-Pro-Ser-Ser-Gly-Ala-Pro-Pro-Pro-Ser-NH$_2$ -continued H-(d-S)-QGTFTSDYSKYLD-Aib-K(PEG$_2$-PEG$_2$-γGlu-CO(CH$_2$)$_{14}$CH$_3$)-RAQDF

VQWLMNTGGPSSGAPPPS-NH$_2$

Compound 34 (SEQ ID NO: 34):
His-(D-Ser)-Gln-Gly-Thr-Phe-Thr-Ser-Asp-Tyr-Ser-Lys-Tyr-Leu-Asp-Lys(PEG$_2$-

PEG$_2$-γGlu-CO(CH$_2$)$_{16}$CO$_2$H)-Arg-Arg-Ala-Gln-Asp-Phe-Val-Gln-Trp-Leu-Met-

Asn-Thr-Gly-Gly-Pro-Ser-Ser-Gly-Ala-Pro-Pro-Pro-Ser-NH$_2$

H-(d-S)-QGTFTSDYSKYLD-K(PEG$_2$-PEG$_2$-γGlu-CO(CH$_2$)$_{16}$CO$_2$H)-RRAQDF

VQWLMNTGGPSSGAPPPS-NH$_2$

Compound 35 (SEQ ID NO: 35):
His-(D-Ser)-Gln-Gly-Thr-Phe-Thr-Ser-Asp-Tyr-Ser-Lys-Tyr-Leu-Asp-Lys(PEG$_2$-

PEG$_2$-CO(CH$_2$)$_{16}$CO$_2$H)-Arg-Arg-Ala-Gla-Asp-Phe-Val-Gln-Trp-Leu-Met-Asn-

Thr-Gly-Gly-Pro-Ser-Ser-Gly-Ala-Pro-Pro-Pro-Ser-NH$_2$

H-(d-S)-QGTFTSDYSKYLD-K(PEG$_2$-PEG$_2$-CO(CH$_2$)$_{16}$CO$_2$H)-RRAQDFVQW

LMNTGGPSSGAPPPS-NH$_2$

Compound 36 (SEQ ID NO: 36):
His-(D-Ser)-Gln-Gly-Thr-Phe-Thr-Ser-Asp-Tyr-Ser-Lys-Tyr-Leu-Asp-Lys(PEG$_2$-

PEG$_2$-γGlu-CO(CH$_2$)$_{16}$CH$_3$)-Arg-Arg-Ala-Gln-Asp-Phe-Val-Gln-Trp-Leu-Met-

Asn-Thr-Gly-Gly-Pro-Ser-Ser-Gly-Ala-Pro-Pro-Pro-Ser-NH$_2$

H-(d-S)-QGTFTSDYSKYLD-K(PEG$_2$-PEG$_2$-γGlu-CO(CH$_2$)$_{16}$CH$_3$)-RRAQDFV

QWLMNTGGPSSGAPPPS-NH$_2$

Compound 37 (SEQ ID NO: 37):
His-(D-Ser)-Gln-Gly-Thr-Phe-Thr-Ser-Asp-Tyr-Ser-Lys-Tyr-Leu-Asp-Lys(PEG$_2$-

PEG$_2$-γGlu-CO(CH$_2$)$_{14}$CH$_3$)-Arg-Arg-Ala-Gln-Asp-Phe-Val-Gln-Trp-Leu-Nle-Asn-

Thr-Gly-Gly-Pro-Ser-Ser-Gly-Ala-Pro-Pro-Pro-Ser-NH$_2$

H-(d-S)-QGTFTSDYSKYLD-K(PEG$_2$-PEG$_2$-γGlu-CO(CH$_2$)$_{14}$CH$_3$)-RRAQDFV

QWL-Nle-NTGGPSSGAPPPS-NH$_2$

Compound 38 (SEQ ID NO: 38):
His-(D-Ser)-Gln-Gly-Thr-Phe-Thr-Ser-Asp-Tyr-Ser-Lys-Tyr-Leu-Asp-Lys(PEG$_2$-

PEG$_2$-γGlu-CO(CH$_2$)$_{16}$CO$_2$H)-Arg-Arg-Ala-Gln-Asp-Phe-Val-Gln-Trp-Leu-Nle-

Asn-Thr-Gly-Gly-Pro-Ser-Ser-Gly-Ala-Pro-Pro-Pro-Ser-NH$_2$

H-(d-S)-QGTFTSDYSKYLD-K(PEG$_2$-PEG$_2$-γGlu-CO(CH$_2$)$_{16}$CO$_2$H)-RRAQDF

VQWL-Nle-NTGGPSSGAPPPS-NH$_2$

Compound 39 (SEQ ID NO: 39):
His-(D-Ser)-Gln-Gly-Thr-Phe-Thr-Ser-Asp-Tyr-Ser-Lys-Tyr-Leu-Asp-Lys(PEG$_2$-

PEG$_2$-γGlu-CO(CH$_2$)$_{16}$CO$_2$H)-Arg-Arg-Ala-Gln-Asp-Phe-Val-Gln-Trp-Leu-Leu-

Asn-Thr-Gly-Gly-Pro-Ser-Ser-Gly-Ala-Pro-Pro-Pro-Ser-NH$_2$

H-(d-S)-QGTFTSDYSKYLD-K(PEG$_2$_PEG$_2$-γGlu-CO(CH$_2$)$_{16}$CO$_2$H)-RRAQDF

VQWLLNTGGPSSGAPPPS-NH$_2$

Compound 40 (SEQ ID NO: 40):
His-(D-Ser)-Gln-Gly-Thr-Phe-Thr-Ser-Asp-Tyr-Ser-Lys-Tyr-Leu-Asp-Lys(PEG$_2$-

PEG$_2$-γGlu-CO(CH$_2$)$_{14}$CH$_3$)-Arg-Arg-Ala-Gln-Asp-Phe-Val-Gln-Trp-Leu-Leu-

Asn-Thr-Gly-Gly-Pro-Ser-Ser-Gly-Ala-Pro-Pro-Pro-Ser-NH$_2$

H-(d-S)-QGTFTSDYSKYLD-K(PEG$_2$-PEG$_2$-γGlu-CO(CH$_2$)$_{14}$CH$_3$)-RRAQDFV

QWLLNTGGPSSGAPPPS-NH$_2$

-continued

Compound 41 (SEQ ID NO: 41):
His-(D-Ser)-Gln-Gly-Thr-Phe-Thr-Ser-Asp-Tyr-Ser-Lys-Tyr-Leu-Asp-Lys(PEG$_2$-PEG$_2$-CO(CH$_2$)$_{16}$CO$_2$H)-Arg-Arg-Ala-Gln-Asp-Phe-Val-Gln-Trp-Leu-Nle-Asn-Thr-Gly-Gly-Pro-Ser-Ser-Gly-Ala-Pro-Pro-Pro-Ser-NH$_2$ H-(d-S)-QGTFTSDYSKYLD-K(PEG$_2$-PEG$_2$-CO(CH$_2$)$_{16}$CO$_2$H)-RRAQDFVQW L-Nle-NTGGPSSGAPPPS-NH$_2$ Compound 42 (SEQ In NO: 42):
His-(D-Ser)-Gln-Gly-Thr-Phe-Thr-Ser-Asp-Tyr-Ser-Lys-Tyr-Leu-Asp-Lys(PEG$_2$-PEG$_2$-CO(CH$_2$)$_{14}$CH$_3$)-Arg-Arg-Ala-Gln-Asp-Phe-Val-Gln-Trp-Leu-Leu-Asn-Thr-Gly-Gly-Pro-Ser-Ser-Gly-Ala-Pro-Pro-Pro-Ser-NH$_2$ H-(d-S)-QGTFTSDYSKYLD-K(PEG$_2$-PEG$_2$-CO(CH$_2$)$_{14}$CH$_3$)-RRAQDFVQWLL NTGGPSSGAPPPS-NH$_2$ Compound 43 (SEQ ID NO: 43):
His-(D-Ser)-Gln-Gly-Thr-Phe-Thr-Ser-Asp-Lys(PEG$_2$-PEG$_2$-γGlu-CO(CH$_2$)$_{14}$CH$_3$)-Ser-Lys-Tyr-Leu-Asp-Aib-Arg-Arg-Ala-Gln-Asp-Phe-Val-Gln-Trp-Leu-Leu-Asn-Thr-Gly-Gly-Pro-Ser-Ser-Gly-Ala-Pro-Pro-Pro-Ser-NH$_2$ H-(d-S)-QGTFTSD-K(PEG$_2$-PEG$_2$-γGlu-CO(CH$_2$)$_{14}$CH$_3$)-SKYLD-Aib-RRAQD FVQWLLNTGGPSSGAPPPS Compound 44 (SEQ ID NO: 44):
His-(D-Ser)-Gln-Gly-Thr-Phe-Thr-Ser-Asp-Lys(PEG$_2$-PEG$_2$-CO(CH$_2$)$_{14}$CH$_3$)-Ser-Lys-Tyr-Leu-Asp-Aib-Arg-Arg-Ala-Gln-Asp-Phe-Val-Gln-Trp-Leu-Leu-Asn-Thr-Gly-Gly-Pro-Ser-Ser-Gly-Ala-Pro-Pro-Pro-Ser-NH$_2$ H-(d-S)-QGTFTSD-K(PEG$_2$-PEG$_2$-CO(CH$_2$)$_{14}$CH$_3$)-SKYLD-Aib-RRAQDFVQ WLLNTGGPSSGAPPPS Compound 45 SEQ ID NO: 45):
His-(D-Ser)-Gln-Gly-Thr-Phe-Thr-Ser-Asp-Lys(PEG$_2$-PEG$_2$-CO(CH$_2$)$_{14}$CH$_3$)-Ser-Lys-Tyr-Leu-Asp-Aib-Arg-Arg-Ala-Gln-Asp-Phe-Val-Gln-Trp-Leu-Nle-Asn-Thr-Gly-Gly-Pro-Ser-Ser-Gly-Ala-Pro-Pro-Pro-Ser-NH$_2$ H-(d-S)-QGTFTSD-K(PEG$_2$-PEG$_2$-CO(CH$_2$)$_{14}$CH$_3$)-SKYLD-Aib-RRAQDFVQ WL-Nle-NTGGPSSGAPPPS Compound 46 SEQ ID NO: 46):
His-(D-Ser)-Gln-Gly-Thr-Phe-Thr-Ser-Asp-Lys(PEG$_2$-PEG$_2$-CO(CH$_2$)$_{16}$CO$_2$H-Ser-Lys-Tyr-Leu-Asp-Aib-Arg-Arg-Ala-Gln-Asp-Phe-Val-Gln-Trp-Leu-Nle-Asn-Thr-Gly-Gly-Pro-Ser-Ser-Gly-Ala-Pro-Pro-Pro-Ser-NH$_2$ H-(d-S)-QGTFTSD-K(PEG$_2$-PEG$_2$-CO(CH$_2$)$_{16}$CO$_2$H)-SKYLD-Aib-RRAQDFVQ WL-Nle-NTGGPSSGAPPPS Compound 47 (SEQ ID NO: 47):
His-(D-Ser)-Gln-Gly-Thr-Phe-Thr-Ser-Asp-Lys(PEG$_2$-PEG$_2$-γGlu-CO(CH$_2$)$_{16}$CO$_2$H)-Ser-Lys-Tyr-Leu-Asp-Aib-Arg-Arg-Ala-Gln-Asp-Phe-Val-Gln-Trp-Leu-Leu-Asn-Thr-Gly-Gly-Pro-Ser-Ser-Gly-Ala-Pro-Pro-Pro-Ser-NH$_2$ H-(d-S)-QGTFTSD-K(PEG$_2$-PEG$_2$-γGlu-CO(CH$_2$)$_{16}$CO$_2$H)-SKYLD-Aib-RRAQ DFATQWLLNTGGPSSGAPPPS Compound 48 (SEQ ID NO: 48):
His-(D-Ser)-Gln-Gly-Thr-Phe-Thr-Ser-Asp-Lys(PEG$_2$-PEG$_2$-γGlu-CO(CH$_2$)$_{16}$CO$_2$H)-Ser-Lys-Tyr-Leu-Asp-Aib-Arg-Arg-Ala-Gln-Asp-Phe-Val-Gln-Trp-Leu-Nle- -continued Asn-Thr-Gly-Gly-Pro-Ser-Ser-Gly-Ala-Pro-Pro-Pro-Ser-NH$_2$ H-(d-S)-QGTFTSD-K(PEG$_2$-PEG$_2$-γGlu-CO(CH$_2$)$_{16}$CO$_2$H)-SKYLD-Aib-RHAQ
DFVQWL-Nle-NTGGPSSGAPPPS The abbreviations used in the invention are defined as follows: Boc is tert-butyloxycarbonyl, Fmoc is fluorenyl-methoxycarbonyl, t-Bu is tert-butyl, ivDDe is 1-(4,4-dimethyl-2,6-dioxo-cyclohexylidene)-3-methyl-butyl removal and lipophilic substituent, resin is resin, TFA is trifluoroacetic acid, EDT is 1,2-ethanedithiol, Phenol is phenol, FBS is fetal bovine serum, BSA is bovine serum albumin, HPLC is high performance liquid chromatography, GLP-1R is glucagon-like peptide-1 receptor, GCGR is glucagon receptor, GLP-1 is glucagon-like peptide, mPEG is monomethoxy-polyethylene diol, OXM is oxyntomodulin, His is histidine, Ser is serine, D-Ser is D-serine, Gln is glutamine, Gly is glycine, Glu is glutamic acid, Ala is alanine acid, Thr is threonine, Lys is lysine, Arg is arginine, Tyr is tyrosine, Asp is aspartic acid, Trp is tryptophan, Phe is phenylalanine, Ile is isoleucine, Leu is leucine, Cys is cysteine, Pro is proline, Val is valine, Met is methionine, Asn is asparagines, HomoLys is homolysine, Orn is ornithine, Dap is diaminopimelic acid, Dab is 2,4-diaminobutyric acid, Nle is norleucine, Aib is 2-aminoisobutyric acid, and AEEA is [2-[2-(amino) ethoxy] ethoxy] acetic acid.

DETAILED DESCRIPTION OF THE INVENTION

Figure 1:
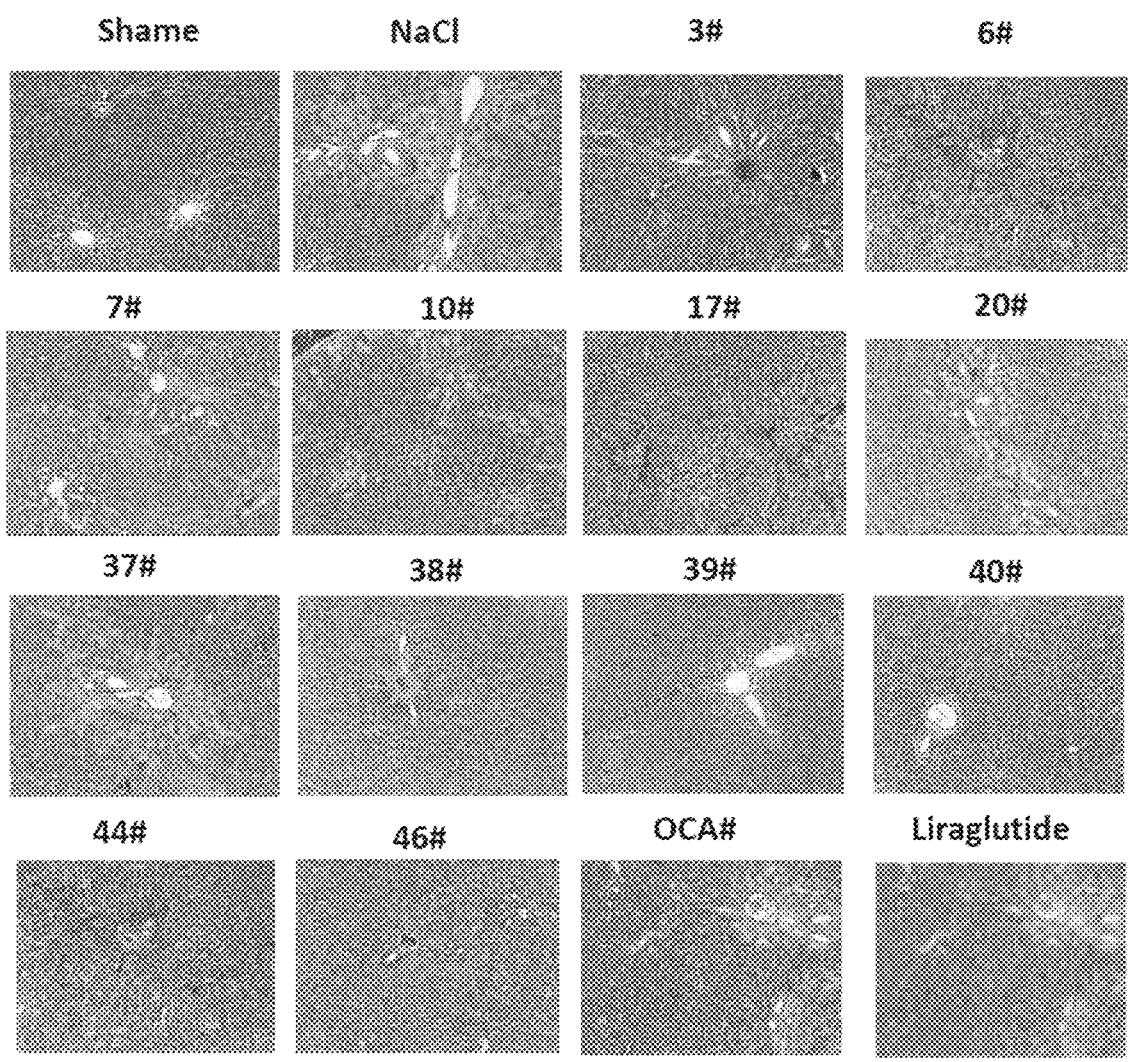
FIG. 1 shows a diagram of HE dyed pathological sections of rat livers.

The embodiments of the invention will be described in detail hereafter in conjunction with the examples, but those skilled in the art will appreciate that the following examples are only intended to indicate the invention and shall not be deemed to define the scope of the invention. Unless otherwise specified, the examples were carried out according to conventional conditions or the conditions recommended by manufacturers. The reagents or instruments used, the manufacture of which were not specified, were all conventional products can be obtained commercially.

Example 1 Synthesis of Polypeptide Compound

Materials:

All amino acids were purchased from NovaBiochem Company. Unless otherwise specified, all other reagents were analytically pure and purchased from Sigma Company. Protein Technologies PRELUDE 6-channel polypeptide synthesizer was used. Phenomenex Luna C18 preparative column (46 mm×250 mm) was used for purification of the polypeptides. High performance liquid chromatograph was manufactured by Waters Company. MS analysis was determined using Agilent mass spectrometer.

Synthetic method of polypeptide compounds of the invention is illustrated by taking the polypeptide compound 6 (SEQ ID NO: 6) as an example: Structure sequence (SEQ ID NO: 6):

His-(D-Ser)-Gln-Gly-Thr-Phe-Thr-Ser-Asp-Tyr-Ser-Lys-Tyr-Leu-Asp-Lys (PEG$_2$-PEG$_2$-γGlu-CO(CH$_2$)$_{14}$CH$_3$)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ a) Main Peptide Chain Assembly:

The following polypeptide in a scale of 0.25 mmol was synthesized on a CS336X peptide synthesizer (CS Bio American Company) according to Fmoc/t-Bu strategy (SEQ ID NO: 6): Boc-His(Boc)-D-Ser(t-Bu)-Gln(OtBu)-Gly-Thr(t-Bu)-Phe-Thr(t-Bu)-Ser(tBu)-Asp(OtBu)-Tyr(t-Bu)-Ser(t-Bu)-Lys(Boc)-Tyr(t-Bu)-Leu-Asp(OtBu)-Lys(ivDde)-Arg (Pbf)-Arg(Pbf)-Ala-Gln(Trt)-Asp(OtBu)-Phe-Val-Gln(Trt)-Trp(Boc)-Leu-Met- Asn(Trt)-Thr(t-Bu)-Gly-Gly-Pro-Ser(t-Bu)-Ser(t-Bu)-Gly-Ala-Pro-Pro-Pro-Ser(t-Bu)-rink amide resin (1) Step 1: 0.75 g of Rink amide MBHA-LL resin (Novabiochem, loading 0.34 mmol/g) was swelled in dichloromethane (DCM) for 1 hour, and the resin was fully washed with N,N-dimethylformamide (DMF) for three times (2) Step 2: The procedure reaction was performed using Rink amide resin as carrier, the mixture of 6-chloro-benzotriazole-1,1,3,3-tetramethyluronium hexafluorophosphate (HCTU), organic base N,N-diisopropylethylamine (DIEPA) at a molar ratio of 1:1 as coupling agent, and N,N-dimethylformamide (DMF) as solvent, the condensation reactions were performed to successively link. Fmoc-Ser(t-Bu)-OH, Fmoc-Pro-OH (3×), Fmoc-Ala-OH, Fmoc-Gly-OH, Fmoc-Ser(t-Bu)-OH (2×), Fmoc-Pro-OH, Fmoc-Gly-OH (2×), Fmoc-Thr(t-Bu)-OH, Fmoc-Asn(Trt)-OH, Fmoc-Met-OH, Fmoc-Leu-OH, Fmoc-Trp(Boc)-OH, Fmoc-Glu(OtBu)-OH, Fmoc-Val-OH, Fmoc-Phe-OH, Fmoc-Asp(OtBu)-OH, Fmoc-Gln(Trt)-OH, Fmoc-Ala-OH, Fmoc-Arg(Pbf)-OH (2×), Fmoc-Lys(ivDde)-OH, Fmoc-Asp(OtBu)-OH, Fmoc-Leu-OH, Fmoc-Tyr(t-Bu)-OH, Fmoc-Lys(Boc)-OH, Fmoc-Ser(t-Bu)-OH, Fmoc-Tyr(t-Bu)-OH, Fmoc-Asp(OtBu)-OH, Fmoc-Ser(t-Bu)-OH, Fmoc-Thr(t-Bu)-OH, Fmoc-Phe-OH, Thr(t-Bu)-OH, Fmoc-Gly-OH, Fmoc-Gln(Trt)-OH, Fmoc-D-Ser(t-Bu)-OH, Boc-His(Boc)-OH to obtain (SEQ ID NO: 6):

Boc-His(Boc)-D-Ser(t-Bu)-Gln(OtBu)-Gly-Thr(t-Bu)-Phe-Thr(t-Bu)-Ser(tBu)-Asp(OtBu)-Tyr(t-Bu)-Ser(t-Bu)-Lys(Boc)-Tyr(t-Bu)-Leu-Asp(OtBu)-Lys(ivDde)-Arg(Pbf)-Arg(Pbf)-Ala-Gln(Trt)-Asp(OtBu)-Phe-Val-Gln(Trt)-Trp(Boc)-Leu-Met- Asn(Trt)-Thr(t-Bu)-Gly-Gly-Pro-Ser(t-Bu)-Ser(t-Bu)-Gly-Ala-Pro-Pro-Pro-Ser(t-Bu)-rink amide resin. Subsequently, the resin was fully washed with N,N-dimethylformamide (DMF), dichloromethane (DCM), Methanol, dichloromethane (DCM), and N,N-dimethylformamide (DMF) in sequence for three times respectively.

In the reaction, 1) the amount of the first amino acid Fmoc-Ser(t-Bu)-OH and the amount of the resin was at a ratio of 1:1-6:1; and 2) in each of the subsequent condensation reactions, each of the amount of Fmoc protected amino acid, 6-chloro-benzotriazole-1,1,3,3-tetramethyluronium hexafluorophosphate (HCTU), organic base N,N-diisopropylethylamine (DIEPA) was excess by 2-8 times, the reaction time was 1-5 hours.

b) Removal of 1-(4,4-dimethyl-2,6-dioxo-cyclohexylidene)-3-methyl-butyl (ivDde) and introduction of lipophilic substituent:

The resin was washed twice in the solution of N,N-dimethylformamide (DMF)/dichloromethane (DCM)=1:1 (volume ratio), and added with freshly prepared 3.0% hydrazine hydrate in N,N-dimethylformamide (DMF). The reaction mixture was shaken at room temperature for 10-30 minutes, and then filtered. The hydrazine treatment step was repeated five times to obtain (SEQ ID NO: 6):

Boc-His(Boc)-D-Ser(t-Bu)-Gln(OtBu)-Gly-Thr(t-Bu)-Phe-Thr(t-Bu)-Ser(tBu)-Asp(OtBu)-Tyr(t-Bu)-Ser(t-Bu)-Lys(Boc)-Tyr(t-Bu)-Leu-Asp(OtBu)-Lys-Arg(Pbf)-Arg(Pbf)-Ala-Gln(Trt)-Asp(OtBu)-Phe-Val-Gln(Trt)-Trp(Boc)-Leu-Met-Asn(Trt)- Thr(t-Bu)-Gly-Gly-Pro-Ser(t-Bu)-Ser(t-Bu)-Gly-Ala-Pro-Pro-Pro-Ser(t-Bu)-rink amide resin. Subsequently, the resin was fully washed with N,N-dimethylformamide (DMF), dichloromethane (DCM), Methanol, dichloromethane (DCM), N,N-dimethylformamide (DMF) in sequence for three times respectively.

Thereto was added an N,N-dimethylformamide (DMF) mixed coupling solution (5 times excess of each) of FmocNH-PEG$_2$-OH (Quanta BioDesign), 2-(7-azo BTA)-N,N,N',N'-tetramethyluronium hexafluorophosphate (HATU) and diisopropylethyl amine (DIEPA), shaken for 2 hours, and filtrated. Subsequently, the resin was fully washed with N,N-dimethylformamide (DMF), dichloromethane (DCM), methanol, dichloromethane (DCM), and N,N-dimethylformamide (DMF) in sequence for three times respectively to obtain (SEQ ID NO: 6):

Boc-His(Boc)-D-Ser(t-Bu)-Gln(OtBu)-Gly-Thr(t-Bu)-Phe-Thr(t-Bu)-Ser(tBu)-Asp(OtBu)-Tyr(t-Bu)-Ser(t-Bu)-Lys(Boc)-Tyr(t-Bu)-Leu-Asp(OtBu)-Lys(Fmoc-PEG$_2$)-Arg(Pbe-Arg(Pbe-Ala-Gln(Trt)-Asp(OtBu)-Phe-Val-Gln(Trt)-Trp(Boc)-Leu-Met-Asn(Trt)-Thr(t-Bu)-Gly-Gly-Pro-Ser(t-Bu)-Ser(t-Bu)-Gly-Ala-Pro-Pro-Pro-Ser(t-Bu)-rink amide resin. Subsequently, the resin was fully washed with N,N-dimethylformamide (DMF), dichloromethane (DCM), methanol, dichloromethane (DCM), N,N-dimethylformamide (DMF) in sequence for three times respectively.

20% piperidine/N,N-dimethylformamide (DMF) solution was used to remove the Fmoc group (30 minutes, repeated removal for twice). Thereto was added an N,N-dimethylformamide (DMF) mixed coupling solution (5 times excess of each) of Fmoc-PEG$_2$-OH, 2-(7-azo BTA)-N,N,N',N'-tetramethyluronium hexafluorophosphate (HATU) and diisopropylethyl amine (DIEPA) to carry out the coupling reaction to obtain (SEQ ID NO: 6):

Boc-His(Boc)-D-Ser(t-Bu)-Gln(OtBu)-Gly-Thr(t-Bu)-Phe-Thr(t-Bu)-Ser(tBu)-Asp(OtBu)-Tyr(t-Bu)-Ser(t-Bu)-Lys(Boc)-Tyr(t-Bu)-Leu-Asp(OtBu)-Lys(Fmoc-PEG$_2$-PEG$_2$)-Arg(Pbe-Arg(Pbe-Ala-Gln(Trt)-Asp(OtBu)-Phe-Val-Gln(Trt)-Trp(Boc)-Leu-Met-Asn(Trt)-Thr(t-Bu)-Gly-Gly-Pro-Ser(t-Bu)-Ser(t-Bu)-Gly-Ala-Pro-Pro-Pro-Ser(t-Bu)-rink amide resin. Subsequently, the resin was fully washed with N,N-dimethylformamide (DMF), dichloromethane (DCM), methanol, dichloromethane (DCM), N,N-dimethylformamide (DMF) in sequence for three times respectively.

20% Piperidine/N,N-dimethylformamide (DMF) solution was used to remove the Fmoc group (30 minutes, repeated removal for twice). Fmoc-γGlu-OtBu was coupled according to conventional conditions in sequence and palmitic acid was added to obtain (SEQ ID NO: 6):

Boc-His(Boc)-D-Ser(t-Bu)-Gln(OtBu)-Gly-Thr(t-Bu)-Phe-Thr(t-Bu)-Ser(tBu)-Asp(OtBu)-Tyr(t-Bu)-Ser(t-Bu)-Lys(Boc)-Tyr(t-Bu)-Leu-Asp(OtBu)-Lys(PEG$_2$-PEG$_2$-C16)-Arg(Pbf)-Arg(Pbf)-Ala-Gln(Trt)-Asp(OtBu)-Phe-Val-Gln(Trt)-Trp(Boc)-Leu-Met-Asn(Trt)-Thr(t-Bu)-Gly-Gly-Pro-Ser(t-Bu)-Ser(t-Bu)-Gly-Ala-Pro-Pro-Pro-Ser(t-Bu)-rink amide resin. The resin was fully washed with N,N-dimethylformamide (DMF), dichloromethane (DCM), methanol and dichloromethane (DCM) in sequence for three times respectively, and dried under vacuum.

c) Removal of polypeptide full protection (SEQ ID NO: 6):

Boc-His(Boc)-D-Ser(t-Bu)-Gln(OtBu)-Gly-Thr(t-Bu)-Phe-Thr(t-Bu)-Ser(tBu)-Asp(OtBu)-Tyr(t-Bu)-Ser(t-Bu)-Lys(Boc)-Tyr(t-Bu)-Leu-Asp(OtBu)-Lys(PEG$_2$-PEG$_2$-C16)-Arg(Pbf)-Arg(Pbf)-Ala-Gln(Trt)-Asp(OtBu)-Phe-Val-Gln(Trt)-Trp(Boc)-Leu-Met-Asn(Trt)-Thr(t-Bu)-Gly-Gly-Pro-Ser(t-Bu)-Ser(t-Bu)-Gly-Ala-Pro-Pro-Pro-Ser(t-Bu)-rink amide resin was added with a cutting fluid TFA/Phenol/thioanisole/EDT/H$_2$O (82.5:5:5:2.5:5, volume ratio) and heated, controlling the temperature of lysate at 25° C., and reacted for 2.5 hours. After filtration, the filter cake was washed with a small amount of lysate for three times, and the filtrates were combined. The filtrate was slowly poured into ice diethyl ether with stirring, placed on standing for more than 2 hours to precipitate completely. The precipitate was centrifuged and washed with ice diethyl ether for three times to obtain crude compound(SEQ ID NO: 6):

```
His-(D-Ser)-Gln-Gly-Thr-Phe-Thr-Ser-Asp-Tyr-Ser-
Lys-Tyr-Leu-Asp-Lys(PEG2-PEG2-γGlu-CO(CH2)14CH3)-
Arg-Arg-Ala-Gln-Asp-Phe-Val-Gln-Trp-Leu-Met-Asn-
Thr-Gly-Gly-Pro-Ser-Ser-Gly-Ala-Pro-Pro-Pro-Ser-
NH2
``` d) Purification of polypeptide compound:

The resulting crude product was dissolved in a solution of acetonitrile (ACN):H$_2$O=1:2 (volume ratio), and purified by preparative HPLC on a 5.0 mm reverse-phase C18-packed 46 mm×250 mm column. 30% acetonitrile (containing 0.05% trifluoroacetic acid)/H$_2$O (containing 0.05% trifluoroacetic acid) were taken as starting materials to elute the column at a gradient (the proportion of acetonitrile is added at a speed of 1.33%/min) and a flow rate of 15 mL/min for 30 minutes, collect the components containing peptide, and lyophilize it so as to obtain a pure product with HPLC purity greater than 95%. The isolated product was analyzed by LC-MS.

Based on the above synthetic steps, the polypeptide compounds synthesized in the invention comprise (Table 1):

TABLE 1

Structure of polypeptide compounds synthesized in the examples of the invention

| (SEQ ID NO:) | Sequence |
|---|---|
| 1 | His-(D-Ser)-Gln-Gly-Thr-Phe-Thr-Ser-Asp-Tyr-Ser-Lys(PEG$_2$-PEG$_2$-γGlu-CO(CH$_2$)$_{14}$CH$_3$)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ |
| 2 | His-(D-Ser)-Gln-Gly-Thr-Phe-Thr-Ser-Asp-Tyr-Ser-Lys(PEG$_2$-PEG$_2$-CO(CH$_2$)$_{16}$CO$_2$H)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ |
| 3 | His-(D-Ser)-Gln-Gly-Thr-Phe-Thr-Ser-Asp-Tyr-Ser-Lys(PEG$_2$-PEG$_2$-CO(CH$_2$)$_{16}$CH$_3$)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ |
| 4 | His-(D-Ser)-Gln-Gly-Thr-Phe-Thr-Ser-Asp-Lys(PEG$_2$-PEG$_2$-γGln-CO(CH$_2$)$_{14}$CH$_3$)-Ser-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ |
| 5 | His-(D-Ser)-Gln-Gly-Thr-Phe-Thr-Ser-Asp-Lys(PEG$_2$-PEG$_2$-γGlu-CO(CH$_2$)$_{16}$CO$_2$H)-Ser-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ |
| 6 | His-(D-Ser)-Gln-Gly-Thr-Phe-Thr-Ser-Asp-Tyr-Ser-Lys-Tyr-Leu-Asp-Lys(PEG$_2$-PEG$_2$-γGlu-CO(CH$_2$)$_{14}$CH$_3$)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ |
| 7 | His-(D-Ser)-Gln-Gly-Thr-Phe-Thr-Ser-Asp-Tyr-Ser-Lys-Tyr-Leu-Asp-Aib-Lys(PEG$_2$-PEG$_2$-γGlu-CO(CH$_2$)$_{16}$CO$_2$H)-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ |
| 8 | His-Aib-Gln-Gly-Thr-Phe-Thr-Ser-Asp-Lys(PEG$_2$-PEG$_2$-γGlu-CO(CH$_2$)$_{14}$CH$_3$)-Ser-Lys-Tyr-Leu-Asp-Aib-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ |
| 9 | His-(D-Ser)-Gln-Gly-Thr-Phe-Thr-Ser-Asp-Tyr-Ser-Lys(PEG$_2$-PEG$_2$-CO(CH$_2$)$_{14}$CH$_3$)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ |
| 10 | His-(D-Ser)-Gln-Gly-Thr-Phe-Thr-Ser-Asp-Tyr-Ser-Lys-Tyr-Leu-Asp-Aib-Lys(PEG$_2$-PEG$_2$-CO(CH$_2$)$_{16}$CO$_2$H)-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ |
| 11 | His-Aib-Gln-Gly-Thr-Phe-Thr-Ser-Asp-Lys(PEG$_2$-PEG$_2$-γGlu-CO(CH$_2$)$_{14}$CO$_2$H)-Ser-Lys-Tyr-Leu-Asp-Aib-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ |
| 12 | His-Aib-Gln-Gly-Thr-Phe-Thr-Ser-Asp-Lys(PEG$_2$-PEG$_2$-γGlu-CO(CH$_2$)$_{16}$CH$_3$)-Ser-Lys-Tyr-Leu-Asp-Aib-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ |
| 13 | His-Aib-Gln-Gly-Thr-Phe-Thr-Ser-Asp-Lys(PEG$_2$-PEG$_2$-γGlu-CO(CH$_2$)$_{14}$CO$_2$H)-Ser-Lys-Tyr-Leu-Asp-Glu-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ |
| 14 | His-Aib-Gln-Gly-Thr-Phe-Thr-Ser-Asp-Lys(PEG$_2$-PEG$_2$-γGlu-CO(CH$_2$)$_{16}$CH$_3$)-Ser-Lys-Tyr-Leu-Asp-Glu-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ |
| 15 | His-Aib-Gln-Gly-Thr-Phe-Thr-Ser-Asp-Lys(PEG$_2$-PEG$_2$-γGlu-CO(CH$_2$)$_{16}$CO$_2$H)-Ser-Lys-Tyr-Leu-Asp-Glu-Arg-Arg-Ala-Gln- |

TABLE 1-continued

Structure of polypeptide compounds synthesized in the examples of the invention

| (SEQ ID NO:) | Sequence |
|---|---|
|  | Asp-Phe-Val-Gln-Trp-Leu-Leu-Asp-Gly-Gly-Pro-Ser-Ser-Gly-Ala-Pro-Pro-Pro-Ser-NH$_2$ |
| 16 | His-Aib-Gln-Gly-Thr-Phe-Thr-Ser-Asp-Lys(PEG$_2$-PEG$_2$-γGlu-CO(CH$_2$)$_{14}$CH$_3$)-Ser-Lys-Tyr-Leu-Asp-Glu-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ |
| 17 | His-(D-Ser)-Gln-Gly-Thr-Phe-Thr-Ser-Asp-Tyr-Ser-Lys-Tyr-Leu-Asp-Ser-Lys(PEG$_2$-PEG$_2$-γGlu-CO(CH$_2$)$_{16}$CO$_2$H)-Ala-Ala-His-Asp-Phe-Val-Glu-Trp-Leu-Leu-Arg-Ala-NH$_2$ |
| 18 | His-(D-Ser)-Gln-Gly-Thr-Phe-Thr-Ser-Asp-Tyr-Ser-Lys-Tyr-Leu-Asp-Gln-Lys-Ala-Ala-Lys(PEG$_2$-PEG$_2$-γGln-CO(CH$_2$)$_{16}$CO$_2$H)-Glu-Phe-Ile-Glu-Trp-Leu-Leu-Arg-Ala-NH$_2$ |
| 19 | His-Aib-Gln-Gly-Thr-Phe-Thr-Ser-Asp-Lys(PEG$_2$-PEG$_2$-γGlu-CO(CH$_2$)$_{16}$CO$_2$H)-Ser-Lys-Tyr-Leu-Asp-Aib-Arg-Arg-Ala-Gln-Asp-Phe-Val-Gln-Trp-Leu-Leu-Asp-Gly-Gly-Pro-Ser-Ser-Gly-Ala-Pro-Pro-Pro-Ser-NH$_2$ |
| 20 | His-(D-Ser)-Gln-Gly-Thr-Phe-Thr-Ser-Asp-Tyr-Ser-Lys(PEG$_2$-PEG$_2$-γGlu-CO(CH$_2$)$_{16}$CO$_2$H)-Lys-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ |
| 21 | His-(D-Ser)-Gln-Gly-Thr-Phe-Thr-Ser-Asp-Tyr-Ser-Lys-Tyr-Leu-Asp-Ser-Lys(PEG$_2$-PEG$_2$-γGlu-CO(CH$_2$)$_{16}$CO$_2$H)-Ala-Ala-His-Asp-Phe-Val-Glu-Trp-Leu-Leu-Asn-Gly-Gly-Pro-Ser-Ser-Gly-Ala-Pro-Pro-Pro-Ser-NH$_2$ |
| 22 | His-(D-Ser)-Gln-Gly-Thr-Phe-Thr-Ser-Asp-Tyr-Ser-Lys-Tyr-Leu-Asp-Ser-Lys(PEG$_2$-PEG$_2$-γGlu-CO(CH$_2$)$_{16}$CH$_3$)-Ala-Ala-His-Asp-Phe-Val-Glu-Trp-Leu-Leu-Asn-Gly-Gly-Pro-Ser-Ser-Gly-Ala-Pro-Pro-Pro-Ser-NH$_2$ |
| 23 | His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-γGlu-CO(CH$_2$)$_{14}$CH$_3$)-Glu-Phe-Ile-Glu-Trp-Leu-Leu-Arg-Ala-NH$_2$ |
| 24 | His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-γGlu-CO(CH$_2$)$_{16}$CH$_3$)-Glu-Phe-Ile-Glu-Trp-Leu-Leu-Arg-Ala-NH$_2$ |
| 25 | His-(D-Ser)-Gln-Gly-Thr-Phe-Thr-Ser-Asp-Tyr-Ser-Lys-Tyr-Leu-Asp-Ser-Lys(PEG$_2$-PEG$_2$-γGlu-CO(CH$_2$)$_{16}$CH$_3$)-Ala-Ala-His-Asp-Phe-Val-Glu-Trp-Leu-Leu-Arg-Ala-NH$_2$ |
| 26 | His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-γGlu-CO(CH$_2$)$_{16}$CO$_2$H)-Glu-Phe-Ile-Glu-Trp-Leu-Leu-Asn-Gly-Gly-Pro-Ser-Ser-Gly-Ala-Pro-Pro-Pro-Ser-NH$_2$ |
| 27 | His-(D-Ser)-Gln-Gly-Thr-Phe-Thr-Ser-Asp-Tyr-Ser-Lys-Tyr-Leu-Asp-Gln-Lys-Ala-Ala-Lys(PEG$_2$-PEG$_2$-γGln-CO(CH$_2$)$_{14}$CO$_2$H)-Glu-Phe-Ile-Glu-Trp-Leu-Leu-Asn-Gly-Gly-Pro-Ser-Ser-Gly-Ala-Pro-Pro-Pro-Ser-NH$_2$ |
| 28 | His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-γGlu-CO(CH$_2$)$_{16}$CH$_3$)-Glu-Phe-Ile-Glu-Trp-Leu-Leu-Asn-Gly-Gly-Pro-Ser-Ser-Gly-Ala-Pro-Pro-Pro-Ser-NH$_2$ |
| 29 | His-(D-Ser)-Gln-Gly-Thr-Phe-Thr-Ser-Asp-Tyr-Ser-Lys-Tyr-Leu-Asp-Glu-Lys-Ala-Ala-Lys(PEG$_2$-PEG$_2$-γGlu-CO(CH$_2$)$_{14}$CH$_3$)-Glu-Phe-Ile-Glu-Trp-Leu-Leu-Asn-Gly-Gly-Pro-Ser-Ser-Gly-Ala-Pro-Pro-Pro-Ser-NH$_2$ |
| 30 | His-(D-Ser)-Gln-Gly-Thr-Phe-Thr-Ser-Asp-Lys(PEG$_2$-PEG$_2$-CO(CH$_2$)$_{16}$CO$_2$H)-Ser-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-NH$_2$ |
| 31 | His-(D-Ser)-Gln-Gly-Thr-Phe-Thr-Ser-Asp-Lys(PEG$_2$-PEG$_2$-CO(CH$_2$)$_{14}$CH$_3$)-Ser-Lys-Tyr-Leu-Asp-Aib-Arg-Arg-Ala-Gln-Asp- |

TABLE 1-continued

Structure of polypeptide compounds synthesized in the examples of the invention

| (SEQ ID NO:) | Sequence |
|---|---|
|  | Phe-Val-Gln-Trp-Leu-Met-Asn-Thr-Gly-Gly-Pro-Ser-Ser-Gly-Ala-Pro-Pro-Pro-Ser-$NH_2$ |
| 32 | His-(D-Ser)-Gln-Gly-Thr-Phe-Thr-Ser-Asp-Lys(PEG$_2$-PEG$_2$-CO(CH$_2$)$_{16}$CH$_3$)-Ser-Lys-Tyr-Leu-Asp-Aib-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-$NH_2$ |
| 33 | His-(D-Ser)-Gln-Gly-Thr-Phe-Thr-Ser-Asp-Tyr-Ser-Lys-Tyr-Leu-Asp-Aib-Lys(PEG$_2$-PEG$_2$-γGlu-CO(CH$_2$)$_{14}$CH$_3$)-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-$NH_2$ |
| 34 | His-(D-Ser)-Gln-Gly-Th-Phe-Thr-Ser-Asp-Tyr-Ser-Lys-Tyr-Leu-Asp-Lys(PEG$_2$-PEG$_2$-γGlu-CO(CH$_2$)$_{16}$CO$_2$H)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-$NH_2$ |
| 35 | His-(D-Ser)-Gln-Gly-Thr-Phe-Thr-Ser-Asp-Tyr-Ser-Lys-Tyr-Leu-Asp-Lys(PEG$_2$-PEG$_2$-CO(CH$_2$)$_{16}$CO$_2$H)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-$NH_2$ |
| 36 | His-(D-Ser)-Gln-Gly-Thr-Phe-Thr-Ser-Asp-Tyr-Ser-Lys-Tyr-Leu-Asp-Lys(PEG$_2$-PEG$_2$-γGlu-CO(CH$_2$)$_{16}$CH$_3$)-Arg-Arg-Ala-Gln-Asp-Phe-Val-Gln-Trp-Leu-Met-Asn-Thr-Gly-Gly-Pro-Ser-Ser-Gly-Ala-Pro-Pro-Pro-Ser-$NH_2$ |
| 37 | His-(D-Ser)-Gln-Gly-Thr-Phe-Thr-Ser-Asp-Tyr-Ser-Lys-Tyr-Leu-Asp-Lys(PEG$_2$-PEG$_2$-γGlu-CO(CH$_2$)$_{14}$CH$_3$)-Arg-Arg-Ala-Gln-Asp-Phe-Val-Gln-Trp-Leu-Nle-Asn-Thr-Gly-Gly-Pro-Ser-Ser-Gly-Ala-Pro-Pro-Pro-Ser-$NH_2$ |
| 38 | His-(D-Ser)-Gln-Gly-Thr-Phe-Thr-Ser-Asp-Tyr-Ser-Lys-Tyr-Leu-Asp-Lys(PEG$_2$-PEG$_2$-γGlu-CO(CH$_2$)$_{16}$CO$_2$H)-Arg-Arg-Ala-Gln-Asp-Phe-Val-Gln-Trp-Leu-Nle-Asn-Thr-Gly-Gly-Pro-Ser-Ser-Gly-Ala-Pro-Pro-Pro-Ser-$NH_2$ |
| 39 | His-(D-Ser)-Gln-Gly-Thr-Phe-Thr-Ser-Asp-Tyr-Ser-Lys-Tyr-Leu-Asp-Lys(PEG$_2$-PEG$_2$-γGlu-CO(CH$_2$)$_{16}$CO$_2$H)-Arg-Arg-Ala-Gln-Asp-Phe-Val-Gln-Trp-Leu-Leu-Asn-Thr-Gly-Gly-Pro-Ser-Ser-Gly-Ala-Pro-Pro-Pro-Ser-$NH_2$ |
| 40 | His-(D-Ser)-Gln-Gly-Thr-Phe-Thr-Ser-Asp-Tyr-Ser-Lys-Tyr-Leu-Asp-Lys(PEG$_2$-PEG$_2$-γGlu-CO(CH$_2$)$_{14}$CH$_3$)-Arg-Arg-Ala-Gln-Asp-Phe-Val-Gln-Trp-Leu-Leu-Asn-Thr-Gly-Gly-Pro-Ser-Ser-Gly-Ala-Pro-Pro-Pro-Ser-$NH_2$ |
| 41 | His-(D-Ser)-Gln-Gly-Thr-Phe-Thr-Ser-Asp-Tyr-Ser-Lys-Tyr-Leu-Asp-Lys(PEG$_2$-PEG$_2$-CO(CH$_2$)16CO2M-Arg-Arg-Ala-Gln-Asp-Phe-Val-Gln-Trp-Leu-Nle-Asn-Thr-Gly-Gly-Pro-Ser-Ser-Gly-Ala-Pro-Pro-Pro-Ser-$NH_2$ |
| 42 | His-(D-Ser)-Gln-Gly-Th-Phe-Thr-Ser-Asp-Tyr-Ser-Lys-Tyr-Leu-Asp-Lys(PEG$_2$-PEG$_2$-CO(CH$_2$)$_{14}$CH$_3$)-Arg-Arg-Ala-Gln-Asp-Phe-Val-Gln-Trp-Leu-Leu-Asn-Thr-Gly-Gly-Pro-Ser-Ser-Gly-Ala-Pro-Pro-Pro-Ser-$NH_2$ |
| 43 | His-(D-Ser)-Gln-Gly-Thr-Phe-Thr-Ser-Asp-Lys(PEG$_2$-PEG$_2$-γGlu-CO(CH$_2$)$_{14}$CH$_3$)-Ser-Lys-Tyr-Leu-Asp-Aib-Arg-Arg-Ala-Gln-Asp-Phe-Val-Gln-Trp-Leu-Leu-Asn-Thr-Gly-Gly-Pro-Ser-Ser-Gly-Ala-Pro-Pro-Pro-Ser-$NH_2$ |
| 44 | His-(D-Ser)-Gln-Gly-Thr-Phe-Thr-Ser-Asp-Lys(PEG$_2$-PEG$_2$-CO(CH$_2$)$_{14}$CH$_3$)-Ser-Lys-Tyr-Leu-Asp-Aib-Arg-Arg-Ala-Gln-Asp-Phe-Val-Gln-Trp-Leu-Leu-Asn-Thr-Gly-Gly-Pro-Ser-Ser-Gly-Ala-Pro-Pro-Pro-Ser-$NH_2$ |
| 45 | His-(D-Ser)-Gln-Gly-Thr-Phe-Thr-Ser-Asp-Lys(PEG$_2$-PEG$_2$-CO(CH$_2$)$_{14}$CH$_3$)-Ser-Lys-Tyr-Leu-Asp-Aib-Arg-Arg-Ala-Gln-Asp-Phe-Val-Gln-Trp-Leu-Nle-Asn-Thr-Gly-Gly-Pro-Ser-Ser-Gly-Ala-Pro-Pro-Pro-Ser-$NH_2$ |
| 46 | His-(D-Ser)-Gln-Gly-Thr-Phe-Thr-Ser-Asp-Lys(PEG$_2$-PEG$_2$-CO(CH$_2$)$_{16}$CO$_2$H)-Ser-Lys-Tyr-Leu-Asp-Aib-Arg-Arg-Ala-Gln- |

TABLE 1-continued

Structure of polypeptide compounds synthesized in the examples of the invention

| (SEQ ID NO:) | Sequence |
|---|---|
|  | Asp-Phe-Val-Gln-Trp-Leu-Nle-Asn-Thr-Gly-Gly-Pro-Ser-Ser-Gly-Ala-Pro-Pro-Pro-Ser-NH$_2$ |
| 47 | His-(D-Ser)-Gln-Gly-Thr-Phe-Thr-Ser-Asp-Lys(PEG$_2$-PEG$_2$-γGlu-CO(CH$_2$)$_{16}$CO$_2$H)-Ser-Lys-Tyr-Leu-Asp-Aib-Arg-Arg-Ala-Gln-Asp-Phe-Val-Gln-Trp-Leu-Leu-Asn-Thr-Gly-Gly-Pro-Ser-Ser-Gly-Ala-Pro-Pro-Pro-Ser-NH$_2$ |
| 48 | His-(D-Ser)-Gln-Gly-Thr-Phe-Thr-Ser-Asp-Lys(PEG$_2$-PEG$_2$-γGlu-CO(CH$_2$)$_{16}$CO$_2$H)-Ser-Lys-Tyr-Leu-Asp-Aib-Arg-Arg-Ala-Gln-Asp-Phe-Val-Gln-Trp-Leu-Nle-Asn-Thr-Gly-Gly-Pro-Ser-Ser-Gly-Ala-Pro-Pro-Pro-Ser-NH$_2$ |

Example 2. In Vitro Inhibition Effect of GLP-1R/GCGR Dual Target Agonist Polypeptides on Hepatic Fibrosis Hepatic stellate cell strain LX-2 was selected to study and observe the effect of different doses of test substances on the expression of LX-2 cell activation marker α-SMA.

Hepatic stellate cell LX-2 was laid on 35 mm cell culture plate, cultured with DMEM (high glucose)+10% FBS+1% double-antibody culture medium (Thermo Fisher), placed overnight when the cells grew to 70% convergence at 37° C. and under the condition of 5% CO$_2$, and treated with the above GLP-1R/GCGR dual target agonist polypeptides 1-48 (dissolved in PBS) for 48 hours the next day morning to extract cell protein, carry out Western Blot, and take β-actin as internal reference and analyze the expression quantities of α-SMA and β-actin by a gray level of Image J 1.50i. PBS with the same volume as that in experimental group was added in negative control.

10 μM of the above polypeptide compounds were treated, and could be able to reduce the expression of α-SMA under all concentrations and had a certain relation between volume and effect; but the negative control had no effect on the expression of α-SMA (Table 2).

Table 2 shows the result of hepatic fibrosis in vitro inhibiting experiment of the selected compounds 1-48 of the invention with a concentration of 10.0 μM, Liraglutide standards (purchased from GL Biochem (Shanghai) Ltd., having a purity greater than 98%, and Liraglutide acetate Cas No.: 204656-20-2) and Exenatide standards (purchased from Hangzhou Peptide Chemical Drug Technology Co., Ltd., having a purity greater than 98%, and Exenatide acetate Cas No.: 141732-76-5). The integrating gray level of α-SMA/β-actin in the negative control group was 100% to analyze the in vitro inhibition activity of hepatic fibrosis of tested polypeptide.

TABLE 2

Effect of compounds 1-48 on relative expression of cell activation marker α-SMA of hepatic stellate cell strain LX-2.

| Polypeptide (SEQ ID NO.) | Concentration (μM) | Relative expression of α-SMA (α-SMA/β-actin, %) |
|---|---|---|
| Negative control | 0 | 100 |
| 1 | 10.0 | 63.5 |
| 2 | 10.0 | 41.62 |
| 3 | 10.0 | 32.25 |
| 4 | 10.0 | 33.50 |
| 5 | 10.0 | 36.04 |
| 6 | 10.0 | 29.19 |
| 7 | 10.0 | 40.52 |
| 8 | 10.0 | 38.25 |
| 9 | 10.0 | 41.86 |
| 10 | 10.0 | 39.49 |
| 11 | 10.0 | 41.78 |
| 12 | 10.0 | 36.99 |
| 13 | 10.0 | 37.93 |
| 14 | 10.0 | 42.80 |
| 15 | 10.0 | 57.29 |
| 16 | 10.0 | 40.35 |
| 17 | 10.0 | 35.38 |
| 18 | 10.0 | 45.60 |
| 19 | 10.0 | 39.75 |
| 20 | 10.0 | 28.39 |
| 21 | 10.0 | 37.66 |
| 22 | 10.0 | 40.56 |
| 23 | 10.0 | 45.91 |
| 24 | 10.0 | 32.42 |
| 25 | 10.0 | 53.34 |
| 26 | 10.0 | 44.44 |
| 27 | 10.0 | 32.34 |
| 28 | 10.0 | 37.62 |
| 29 | 10.0 | 49.36 |
| 30 | 10.0 | 55.53 |
| 31 | 10.0 | 36.89 |
| 32 | 10.0 | 37.14 |
| 33 | 10.0 | 35.45 |
| 34 | 10.0 | 38.18 |
| 35 | 10.0 | 51.28 |
| 36 | 10.0 | 42.49 |
| 37 | 10.0 | 29.95 |
| 38 | 10.0 | 40.55 |
| 39 | 10.0 | 41.68 |
| 40 | 10.0 | 37.55 |
| 41 | 10.0 | 42.10 |
| 42 | 10.0 | 38.11 |
| 43 | 10.0 | 42.34 |
| 44 | 10.0 | 39.19 |
| 45 | 10.0 | 32.22 |
| 46 | 10.0 | 36.84 |
| 47 | 10.0 | 40.36 |
| 48 | 10.0 | 43.25 |
| Liraglutide | 10.0 | 78.4 |
| Exenatide | 10.0 | 83.2 |

It can be seen from Table 2 that the dual target agonist polypeptide compounds 1-48 of the invention all indicate the expression of excellent in vitro inhibiting LX-2 cell activation marker α-SMA compared with GLP-1 analogue Liraglutide and Exenatide. Wherein, the compounds 3, 6, 7, 10, 17, 20, 37, 38, 39, 40, 44, 46, Obeticholic Acid (CAS: 459789-99-2, purchased from Zhejiang Warrant Pharmaceutical Co., Ltd.) and Liraglutide are selected to make further zoological evaluation in vivo.

Example 3. Functions of GLP-1R/GCGR Dual Target Agonist Polypeptides to Improve and Treat Bile Duct Ligation (BDL)-Induced Hepatic Fibrosis in Rats (Biliary Cirrhosis Rat Model)

1. Experimental Drugs: polypeptide compounds 3, 6, 7, 10, 17, 20, 37, 38, 39, 40, 44, 46, Obeticholic Acid (Abbr. OCA, CAS:459789-99-2, purchased from Zhejiang Warrant Pharmaceutical Co., Ltd.) and Liraglutide. Saving condition was −20° C.

2. Experimental Method:

128 male SD rats with body weight of 200-230 g were randomly divided into sixteen groups, which were respectively:

1) Sham-operated group (Shame group with only free common bile duct, no ligation, n=8);
2) BDL+ normal saline control group (NaCl group, subcutaneous injection normal saline after BDL operation, n=8);
3) BDL+3 (50 μg/Kg) group (subcutaneous injection with 50 μg/Kg after BDL operation, n=8);
4) BDL+6 (50 μg/Kg) group (subcutaneous injection with 50 μg/Kg after BDL operation, n=8);
5) BDL+7 (50 μg/Kg) group (subcutaneous injection with 50 μg/Kg after BDL operation, n=8);
6) BDL+10 (50 μg/Kg) group (subcutaneous injection with 50 μg/Kg after BDL operation, n=8);
7) BDL+17 (50 μg/Kg) group (subcutaneous injection with 50 μg/Kg after BDL operation, n=8);
8) BDL+20 (50 μg/Kg) group (subcutaneous injection with 50 μg/Kg after BDL operation, n=8);
9) BDL+37 (50 μg/Kg) group (subcutaneous injection with 50 μg/Kg after BDL operation, n=8);
10) BDL+38 (50 μg/Kg) group (subcutaneous injection with 50 μg/Kg after BDL operation, n=8);
11) BDL+39 (50 μg/Kg) group (subcutaneous injection with 50 μg/Kg after BDL operation, n=8);
12) BDL+40 (50 μg/Kg) group (subcutaneous injection with 50 μg/Kg after BDL operation, n=8);
13) BDL+44 (50 μg/Kg) group (subcutaneous injection with 50 μg/Kg after BDL operation, n=8);
14) BDL+46 (50 μg/Kg) group (subcutaneous injection with 50 μg/Kg after BDL operation, n=8);
15) BDL+OCA (7.5 mg/Kg) group (intraperitoneal injection with 7.5 mg/Kg after BDL operation, n=8);
16) BDL+Liraglutide (50 μg/Kg) group (subcutaneous injection with 50 μg/Kg after BDL operation, n=8).

SD rats with body weight of 200-230 g at SPF level were provided by Lanzhou University Laboratory Animal Center. After rats were quarantined in the room (SPF environment) for one week, model rat and rat in sham-operated group were subject to intraperitoneal injection and anesthesia with 0.6% pentobarbital sodium solution, and operation was performed on a super clean bench after anesthesia. Bilateral ligation was conducted on model rat after the common bile duct was separated, and ligation was not conducted on rat in sham-operated group, but only the common bile duct was separated. Administration was started from the next day of the operation.

Administration was started from the first day of the operation, and subcutaneous injection of compounds 3, 6, 7, 10, 17, 20, 37, 38, 39, 40, 44, 46 and Liraglutide with 50 μg/kg was performed every two days; intraperitoneal injection for the Obeticholic Acid administration group with 7.5 mg/kg was performed every day; as for the normal saline group, injection was performed every day. During the administration, changes in vital signs of rats were observed every day.

After the end of two weeks of administration cycle (14 days), the rats were killed to collect materials for subsequent biological determination experiments. The livers were taken out for HE dye, Sirius Red dye and IHC dye. Image-pro plus and Graph pad software were used for statistics.

Figure 2:
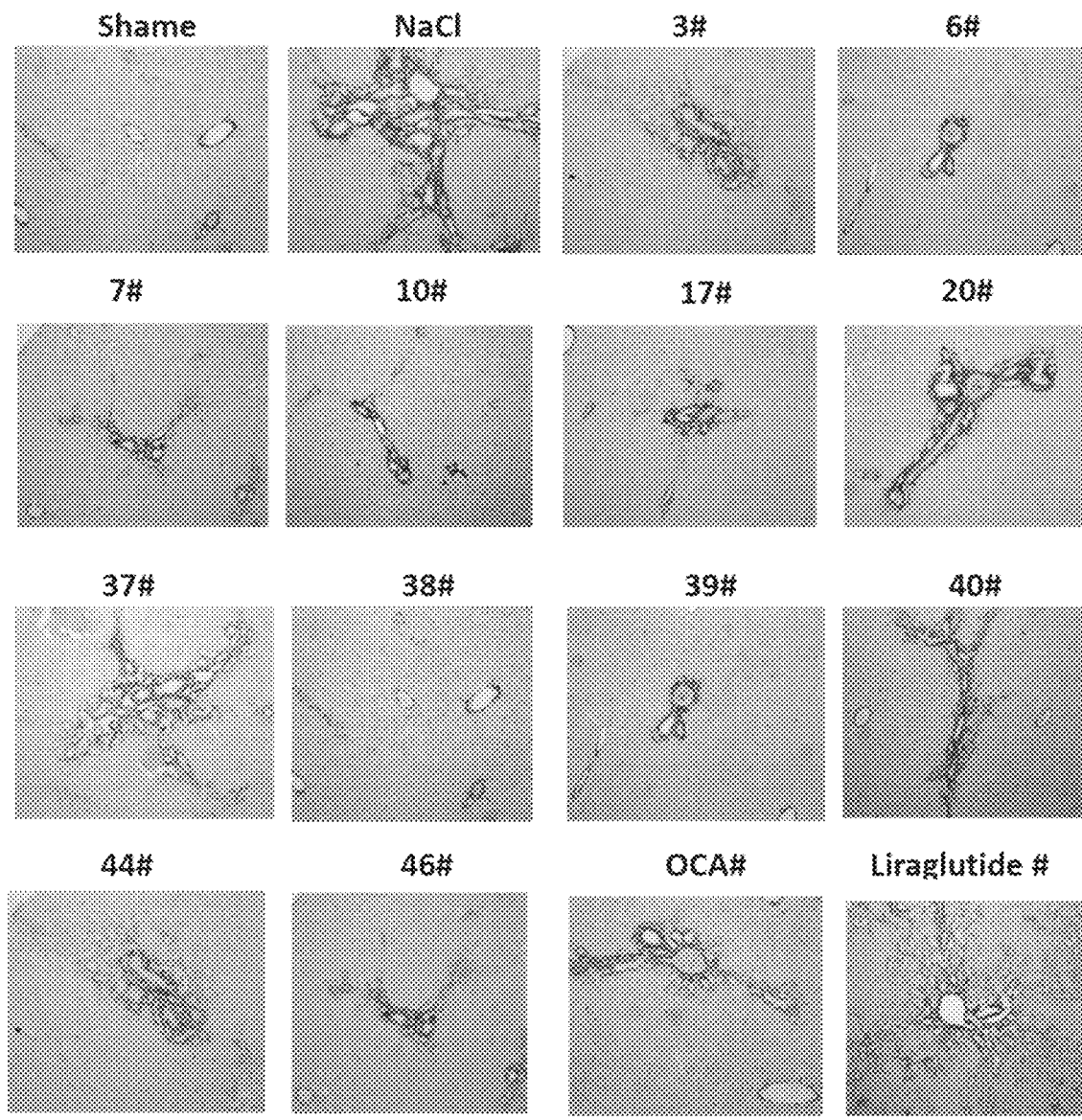
FIG. 2 shows a diagram of Sirius Red dyed pathological sections of rat livers.
Figure 3:
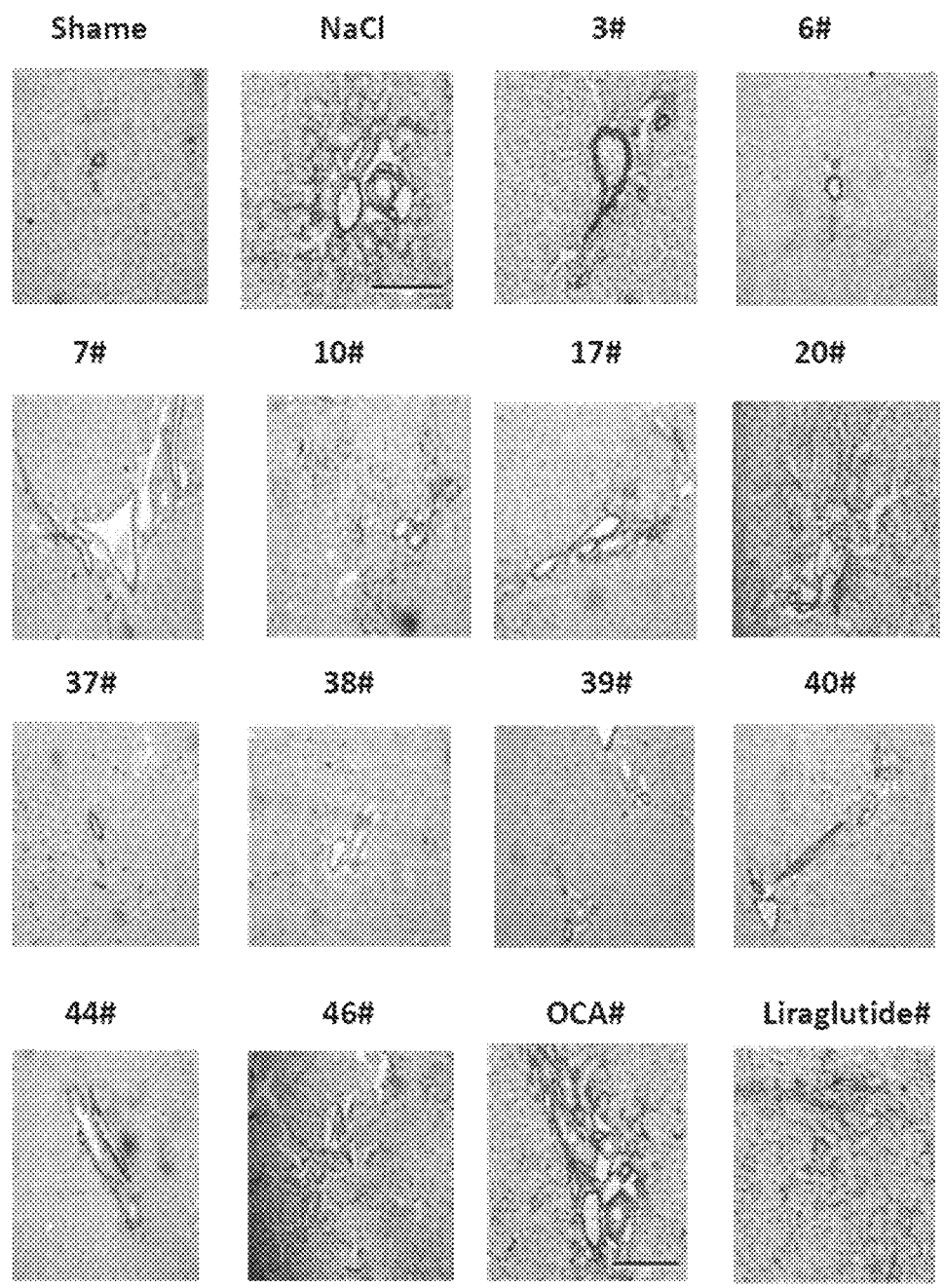
FIG. 3 shows a diagram of IHC dyed pathological sections of rat livers.
Figure 4:
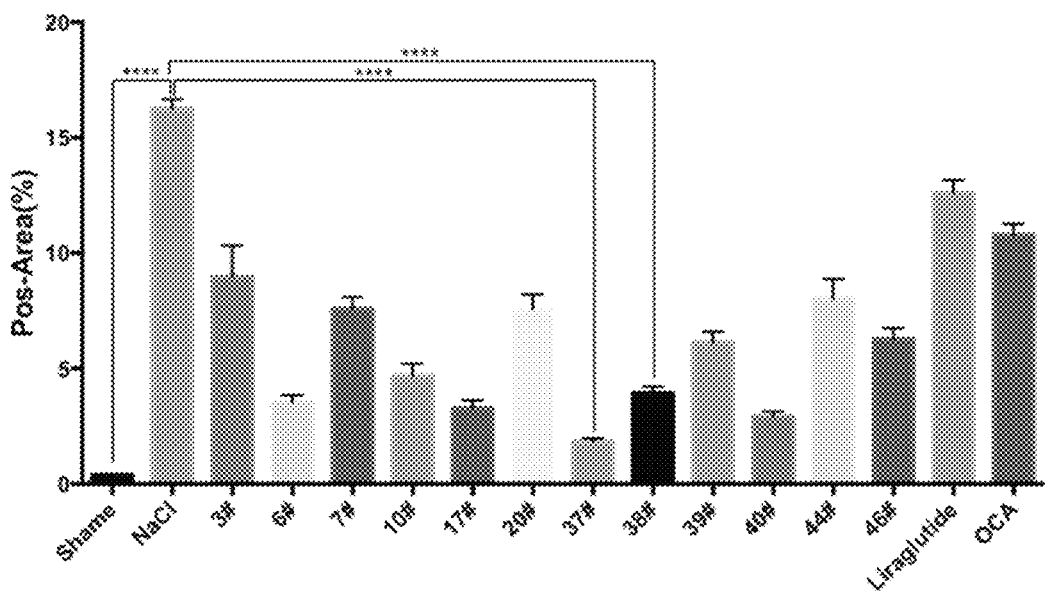
FIG. 4 shows a statistic histogram of the Sirius Red dyed pathological sections of rat livers (**** represents within a confidence (p<0.0001) of 99% compared with the control group).
Figure 5:
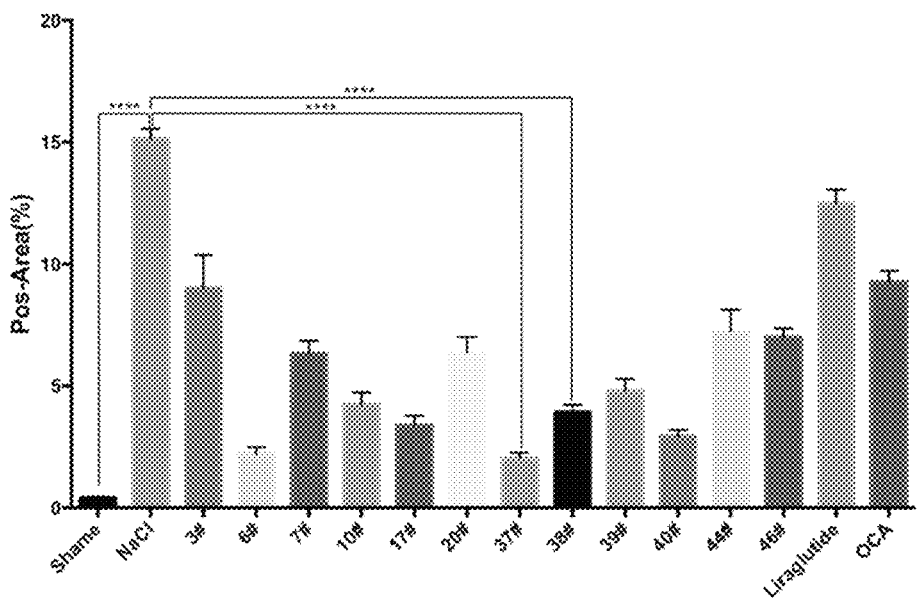
FIG. 5 shows a α-SMA statistic histogram of the IHC dyed pathological sections of rat livers (**** represents within a confidence (p<0.0001) of 99% compared with the control group).

Results of HE dyed pathological sections in FIG. 1, Sirius Red dyed pathological sections in FIG. 2, IHC dyed pathological sections in FIG. 3 of rat livers, and statistics in FIGS. 4 and 5 show that the BDL normal saline administration control group (NaCl group) has inflammatory cell infiltration around a central vein area, hepatic cells have edema and denaturation, and the portal area and hepatic lobule septum have a large amount of collagenous fiber deposition. Polypeptide compounds 3, 6, 7, 10, 17, 20, 37, 38, 39, 40, 44 and 46 administration groups significantly inhibit collagenous fiber deposition, and can significantly reduce BDL-induced hepatic fibrosis and inflammation in mice. It shows that as compared with liraglutide and exenatide, the polypeptide compounds 3, 6, 7, 10, 17, 20, 37, 38, 39, 40, 44 and 46 can obviously treat and improve the degree of BDL-induced cholestasis hepatic fibrosis in rats.

The α-SMA immunization group in the hepatic cells expresses that α-SMA protein immunohistochemical positive staining is expressed in hepatic sinusoidal fibroblast cytoplasm in a fibrous septum of the portal area and near the fibrous septum. The polypeptide compounds 3, 6, 7, 10, 17, 20, 37, 38, 39, 40, 44 and 46 administration groups significantly inhibit α-SMA. Pharmaceutical effects of the polypeptide compounds 3, 6, 7, 10, 17, 20, 37, 38, 39, 40, 44 and 46 are obviously better than liraglutide and exenatide.

Figure 6:
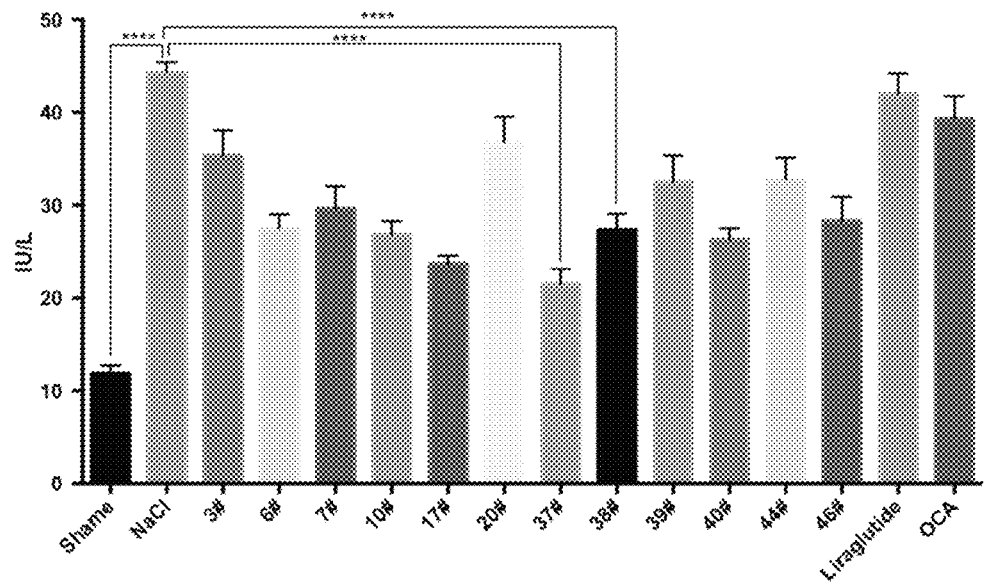
FIG. 6 shows a statistic histogram of determined content of glutamic-pyruvic transaminase (ALT) of serum indicator of rats (**** represents within a confidence (p<0.0001) of 99% compared with the control group).

According to analyses on the serum indicator, results of statistics FIG. 6 show that the polypeptide compounds 3, 6, 7, 10, 17, 20, 37, 38, 39, 40, 44 and 46 significantly inhibit ALT in the serum.

Figure 7:
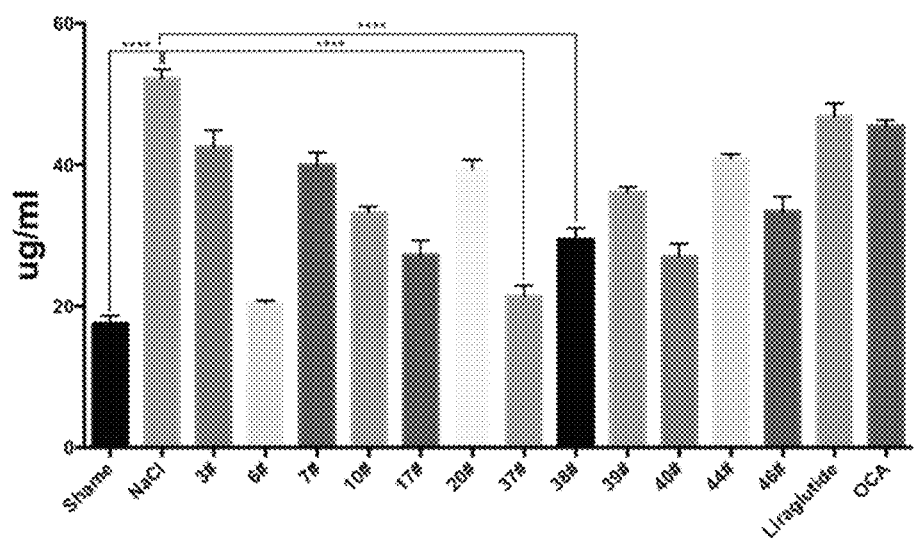
FIG. 7 shows a statistic histogram of determined content of hydroxyproline (HYP) of hepatic tissue of rats (**** represents within a confidence (p<0.0001) of 99% compared with the control group).

In the stage of hepatic fibrosis, the mainly increased component within the liver is collagenous fiber, and hydroxyproline is specific to collagenous fiber, so determining the content of hydroxyproline may be converted into the content of hepatic collagen to reflect the degree of hepatic fibrosis. Determination of hydroxyproline in the hepatic cells may reflect situations of collagen degradation. According to analyses on the content of hydroxyproline of liver tissues, results of statistics FIG. 7 show that the polypeptide compounds 3, 6, 7, 10, 17, 20, 37, 38, 39, 40, 44 and 46 significantly inhibit the content of hydroxyproline of the liver.

In conclusion, the results of the above experiments show that the polypeptide compounds 3, 6, 7, 10, 17, 20, 37, 38, 39, 40, 44 and 46 can obviously treat and improve the degree of BDL-induced cholestasis hepatic fibrosis in rats, and has significant therapeutic effects on diseases such as biliary cirrhosis. The dual target agonist polypeptides are applicable to the prevention or treatment of biliary cirrhosis and related hepatic fibrosis diseases.

What is claimed is:

1. A method of preventing or treating biliary cirrhosis diseases or related hepatic fibrosis course in a subject, the method comprising:

administering to the subject at least one oxyntomodulin analogue GLP-1R/GCGR dual target agonist polypeptide, wherein the polypeptides comprise a parent peptide represented by the following amino acid sequence (SEQ ID NO:49):

His-Xaa2-Gln-Gly-Thr-Phe-Thr-Ser-Asp-Xaa10-Ser-Lys-Xaa13-Leu-Asp-Xaa16-Xaa17-Xaa18-Ala-Xaa20-Xaa21-Phe-Xaa23-Xaa24-Trp-Leu-Xaa27-Xaa28-Xaa29-Xaa30-Xaa31-Xaa32-Xaa33-Xaa34-Xaa35-Xaa36-Xaa37-Xaa38-Xaa39-Xaa40-COR$_1$ wherein, R$_1$=—NH$_2$;
Xaa2=D-Ser;
Xaa10=Lys or Tyr;
Xaa13=Lys or Tyr;
Xaa16=Aib, or Lys;
Xaa17 Arg;
Xaa18=Arg;
Xaa20=Gln;
Xaa21=Asp;
Xaa23=Val;
Xaa24=Gln;
Xaa27=Met, Leu or Nle;
Xaa28=Asn or Arg;
Xaa29=Thr or is absent;
Xaa30=Gly;
Xaa31=Gly;
Xaa32=Pro;
Xaa33=Ser;
Xaa34=Ser;
Xaa35=Gly;

Xaa36=Ala;
Xaa37=Pro;
Xaa38=Pro;
Xaa39=Pro;
Xaa40=Ser;
wherein at least one of Xaa10, Xaa16, Xaa17 or Xaa20 is Lys, the side chain of the at least one Lys or the Lys at position 12 of the sequence is attached to a lipophilic substituent in such a way that a carboxyl group of the lipophilic substituent forms an amide bond with an amino of a bridging group, the bridging group is attached to the parent peptide by means of a carboxyl group of the amino acid residue of the bridging group which forms an amide bond with a N-terminal residue of Lys of the parent peptide, the bridging group is Glu, Asp and/or $(PEG)_m$, wherein m is an integer of 2-10; the lipophilic substituent is an acyl group selected from $CH_3(CH_2)_nCO-$ or $HOOC(CH_2)_nCO-$, wherein n is an integer of 10-24, wherein when the position 10, 12, 16, 17, or 20 of the amino acid sequence is Lys, the lipophilic substituent attached to the side chain of the Lys is one of the following structures:

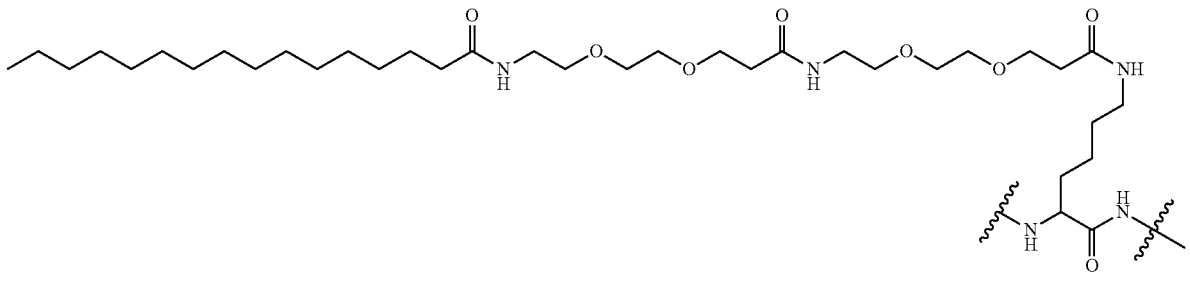

Lys(PEG$_2$-PEG$_2$-CO(CH$_2$)$_{14}$CH$_3$)

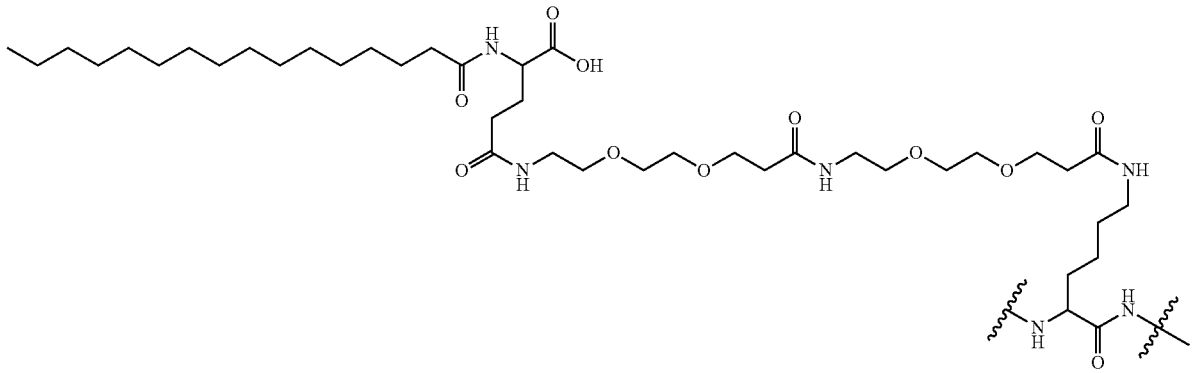

Lys(PEG$_2$-PEG$_2$-γ Glu-CO(CH$_2$)$_{14}$CH$_3$)

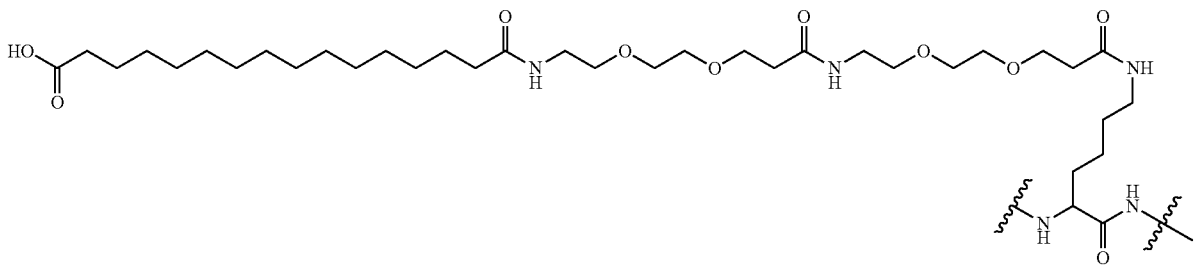

Lys(PEG$_2$-PEG$_2$-CO(CH$_2$)$_{14}$CO$_2$H)

-continued
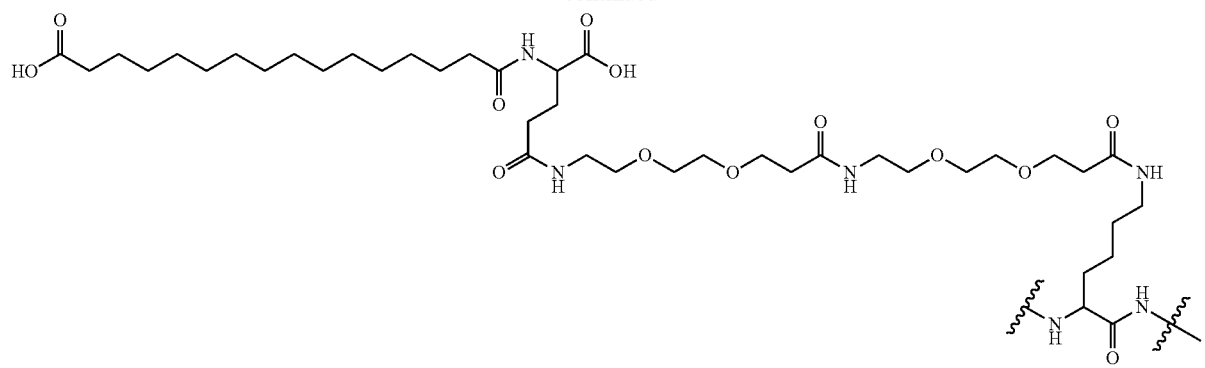
Lys(PEG₂-PEG₂-γ Glu-CO(CH₂)₁₄CO₂H)
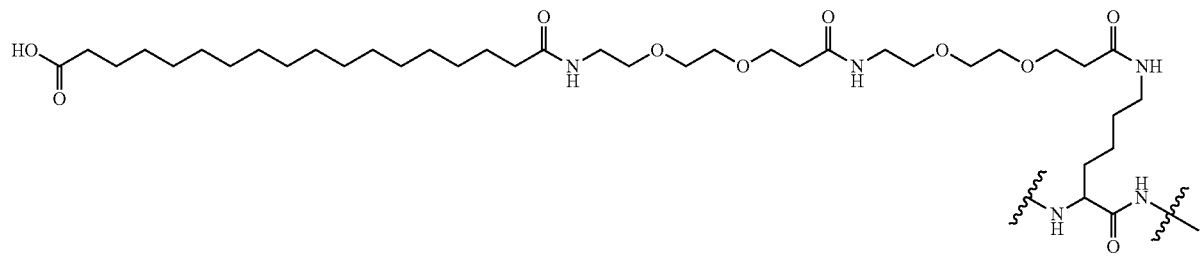
Lys(PEG₂-PEG₂-CO(CH₂)₁₆CO₂H)
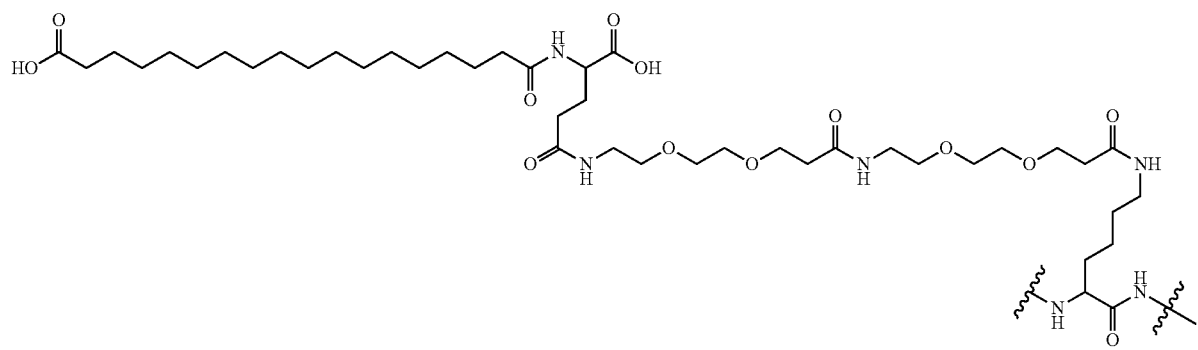
Lys(PEG₂-PEG₂-γ Glu-CO(CH₂)₁₆CO₂H)
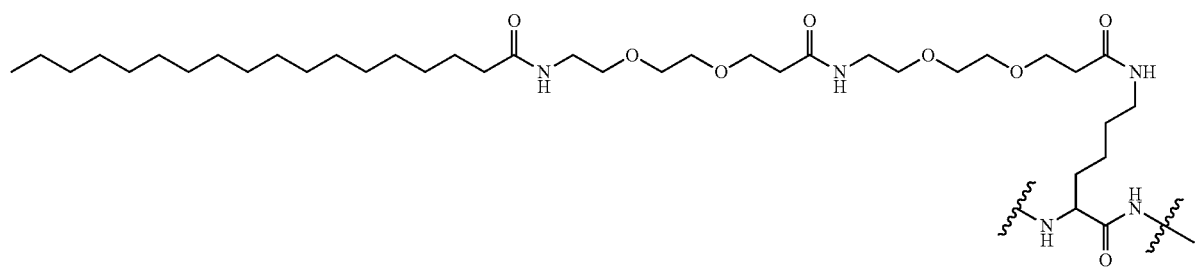
Lys(PEG₂-PEG₂-CO(CH₂)₁₆CH₃)

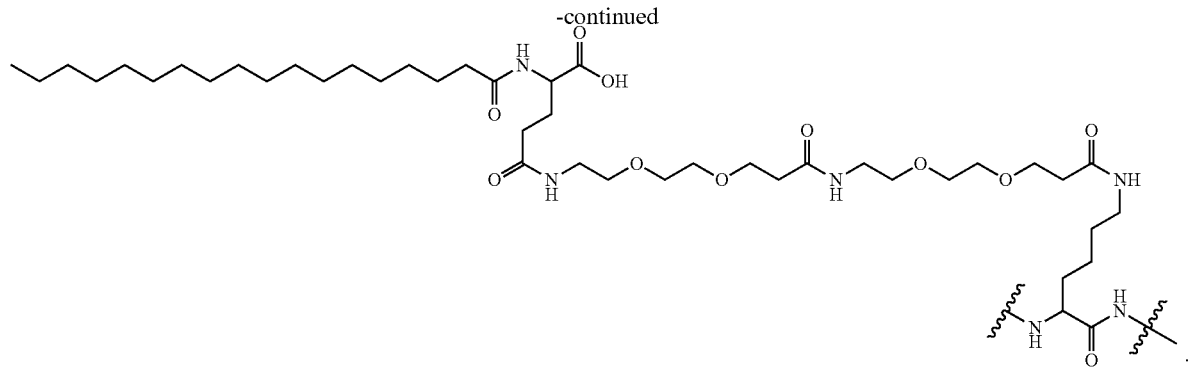

Lys(PEG$_2$-PEG$_2$-γ Glu-CO(CH$_2$)$_{16}$CH$_3$)

2. The method according to claim 1, wherein the bridging group is Glu-(PEG)$_m$ or Asp-(PEG)$_m$ or (PEG)$_m$.

3. The method according to claim 1, wherein a molecular bridge is formed by means of the bridging group between the side chains of amino acid residue pairs 12 and 16, 16 and 20, 17 and 21, or 20 and 24 in the amino acid sequence.

4. The method according to claim 1, wherein the Lys attached to the lipophilic substituent is replaced with Homo-Lys, Orn, Dap or Dab.

5. The method according to claim 1, wherein the amino acid sequence of the parent peptide is selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17 and SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO: 40, SEQ ID NO:41, SEQ ID NO:42, SEQ ID NO:43, SEQ ID NO:44, SEQ ID NO:45, SEQ ID NO:46, SEQ ID NO:47 and SEQ ID NO:48.

6. The method according to claim 1, comprising an effective amount of at least one polypeptide and at least one pharmaceutically acceptable pharmaceutical carrier in preparing a pharmaceutical composition of the oxyntomodulin analogue GLP-1R/GCGR dual target agonist polypeptides, and formulating into various suitable dosage forms.

7. The method according to claim 1, comprising an effective amount of at least one polypeptide and at least one pharmaceutically acceptable pharmaceutical carrier in preparing a pharmaceutical composition of the oxyntomodulin analogue GLP-1R/GCGR dual target agonist polypeptides, and formulating into various suitable dosage forms.

8. The method according to claim 2, comprising an effective amount of at least one polypeptide and at least one pharmaceutically acceptable pharmaceutical carrier in preparing a pharmaceutical composition of the oxyntomodulin analogue GLP-1R/GCGR dual target agonist polypeptides, and formulating into various suitable dosage forms.

9. The method according to claim 3, comprising an effective amount of at least one polypeptide and at least one pharmaceutically acceptable pharmaceutical carrier in preparing a pharmaceutical composition of the oxyntomodulin analogue GLP-1R/GCGR dual target agonist polypeptides, and formulating into various suitable dosage forms.

10. The method according to claim 4, comprising an effective amount of at least one polypeptide and at least one pharmaceutically acceptable pharmaceutical carrier in preparing a pharmaceutical composition of the oxyntomodulin analogue GLP-1R/GCGR dual target agonist polypeptides, and formulating into various suitable dosage forms.

11. The method according to claim 5, comprising an effective amount of at least one polypeptide and at least one pharmaceutically acceptable pharmaceutical carrier in preparing a pharmaceutical composition of the oxyntomodulin analogue GLP-1R/GCGR dual target agonist polypeptides, and formulating into various suitable dosage forms.

* * * * *